(12) United States Patent
Hargadon

(10) Patent No.: US 7,712,468 B2
(45) Date of Patent: May 11, 2010

(54) MAGNETIC DENTAL APPLIANCE

(76) Inventor: Paul K. Hargadon, 274 Second Avenue, Ottawa, ON (CA) K1S-2H9

( * ) Notice: Subject to any disclaimer, the term of this patent is extended or adjusted under 35 U.S.C. 154(b) by 397 days.

(21) Appl. No.: 11/677,198

(22) Filed: Feb. 21, 2007

(65) Prior Publication Data

US 2008/0199824 A1    Aug. 21, 2008

(51) Int. Cl.
*A61F 5/56* (2006.01)
*A61C 3/00* (2006.01)

(52) U.S. Cl. .............................. 128/848; 433/6; 433/24

(58) Field of Classification Search ................... 128/848
See application file for complete search history.

(56) References Cited

U.S. PATENT DOCUMENTS

| | | | |
|---|---|---|---|
| 4,184,252 A * | 1/1980 | Krol et al. ................... 433/172 |
| 4,396,373 A | 8/1983 | Dellinger |
| 4,519,386 A | 5/1985 | Sullivan |
| 4,671,766 A | 6/1987 | Norton |
| 4,671,767 A | 6/1987 | Blechman et al. |
| 4,828,113 A * | 5/1989 | Friedland et al. ............. 206/570 |
| 4,871,310 A * | 10/1989 | Vardimon ..................... 433/19 |
| 5,013,243 A | 5/1991 | Tanaka et al. |
| 5,085,584 A | 2/1992 | Boyd |
| 5,092,346 A | 3/1992 | Hays et al. |
| 5,117,816 A | 6/1992 | Shapiro et al. |
| 5,203,701 A | 4/1993 | Burtch |
| 5,365,945 A | 11/1994 | Halstrom |
| 5,409,017 A * | 4/1995 | Lowe ......................... 128/848 |
| 5,427,117 A | 6/1995 | Thornton |
| 5,499,633 A | 3/1996 | Fenton |
| 5,566,683 A | 10/1996 | Thornton |
| 5,611,355 A | 3/1997 | Hilsen |
| 5,678,998 A | 10/1997 | Honkura et al. |
| 5,884,628 A | 3/1999 | Hilsen |
| 5,954,506 A * | 9/1999 | Tanaka ........................ 433/214 |
| 6,055,986 A * | 5/2000 | Meade ......................... 128/848 |

(Continued)

FOREIGN PATENT DOCUMENTS

EP    1095629    6/2006

OTHER PUBLICATIONS

Bondmark et al., "Long-term effects of orthodontic magnets on human buccal mucosa: a clinical, histological and immunohistochemical study", European Journal of Orthodontics, 1998, vol. 20, pp. 211-218.

(Continued)

*Primary Examiner*—Patricia M Bianco
*Assistant Examiner*—Victoria Hicks
(74) *Attorney, Agent, or Firm*—Kathleen E. Marsman; Borden Ladner Gervais LLP

(57) ABSTRACT

A removable magnetic dental appliance is provided. The magnetic dental appliance can be used in the treatment of various conditions, including but not limited to, snoring, sleep apnea, some forms of temporomandibular joint pain or inflammation, myofascial pain or bruxism. The appliance includes an upper arch attachment member and a lower arch attachment member, each for removably engaging at least a portion of the dentition. A magnetic component is positioned anteriorly on one of the upper arch attachment member or the lower arch attachment member and a non-magnet magnet-attracted element is provided on the other arch attachment member for magnetic engagement with the magnetic component when the upper and lower arch attachment members are substantially vertically aligned. The appliance uses magnetic force to selectively position the mandible while still permitting movement of the mandible relative to the maxilla for improved comfort.

19 Claims, 13 Drawing Sheets

U.S. PATENT DOCUMENTS

| | | | |
|---|---|---|---|
| 6,129,084 | A | 10/2000 | Bergersen |
| 6,206,192 | B1 * | 3/2001 | Winstead et al. ............ 206/572 |
| 6,299,450 | B1 | 10/2001 | Honkura et al. |
| 6,305,376 | B1 | 10/2001 | Thornton |
| 6,447,294 | B1 * | 9/2002 | Price ......................... 433/167 |
| 6,659,771 | B2 * | 12/2003 | Honkura et al. ............ 433/189 |
| 6,845,774 | B2 * | 1/2005 | Gaskell ...................... 128/848 |
| 6,857,429 | B2 | 2/2005 | Eubank |
| 2003/0217753 | A1 | 11/2003 | Thornton |
| 2009/0014013 | A1 * | 1/2009 | Magnin ...................... 128/848 |

OTHER PUBLICATIONS

Noar and Evans, "Rare Earth Magnets in Orthodontics: An Overview", British Journal of Orthodontics, 1999, vol. 26 (1), pp. 29-37.

Bernhold M, et al. "A Magnetic Appliance For Treatment of Snoring Patients with and without Obstructive Sleep Apnea", Am J Orthod Dentofacial Orthop, 1998, vol. 113(2), pp. 144-155.

Lowe, "Oral Appliances for Sleep Breathing Disorders", Kryger, Roth and Dement (eds), Principles and Practice of Sleep Medicine (3rd Ed.), Philadelphia, PA, WB Saunders, 2001, pp. 929-939.

Ivanhoe and Attanasio, "Sleep Disorders and Oral Appliances", Attanasio and Bailey (eds), Dental Clinics of North America: Sleep Disorders: Dentistry's Role, vol. 45(4), Oct. 2001, pp. 733-758.

* cited by examiner

Fig. 4
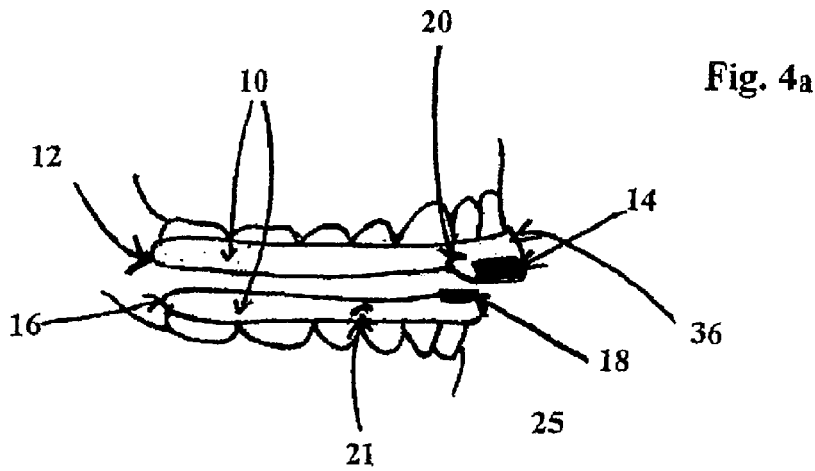
Fig. 4a
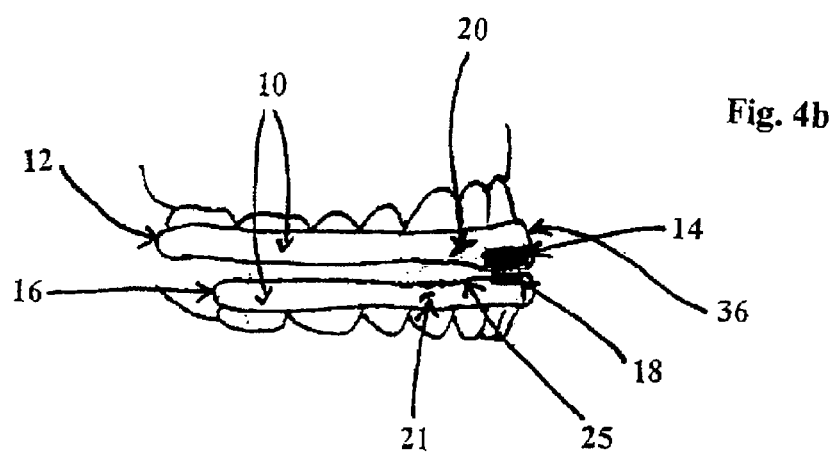
Fig. 4b
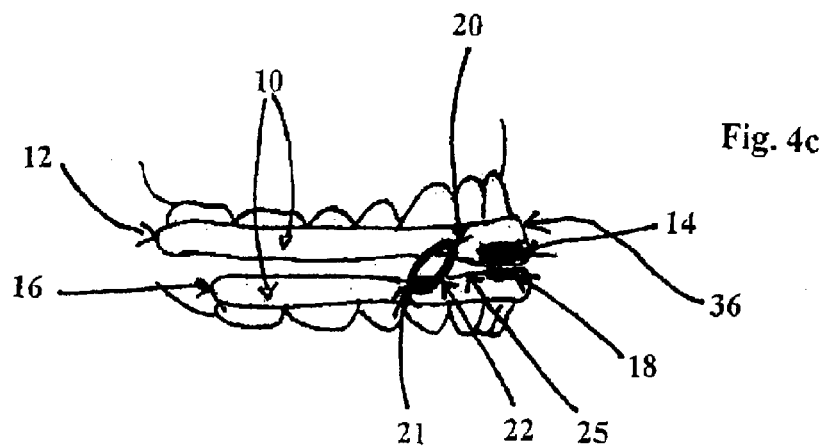
Fig. 4c

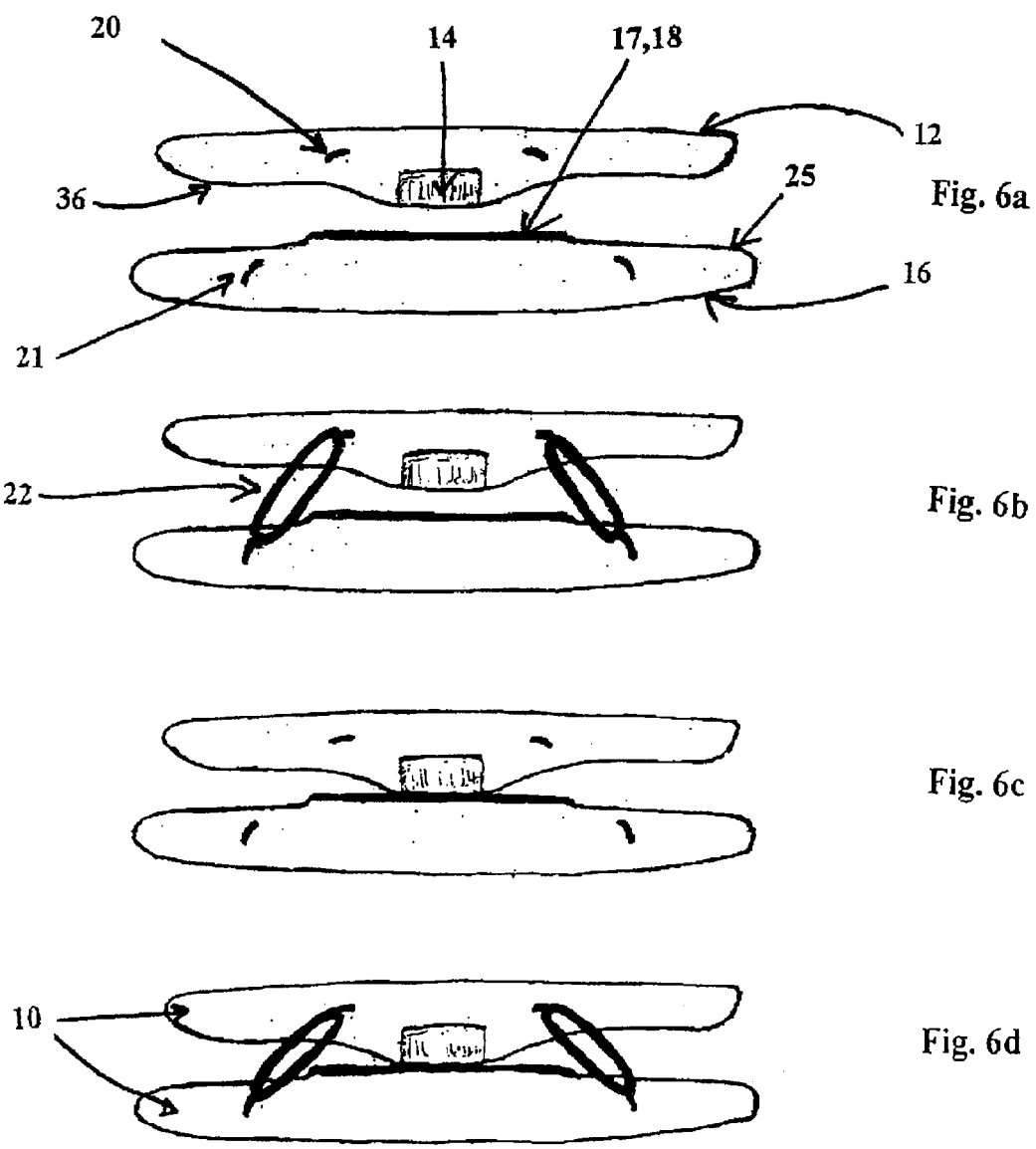

Fig. 9
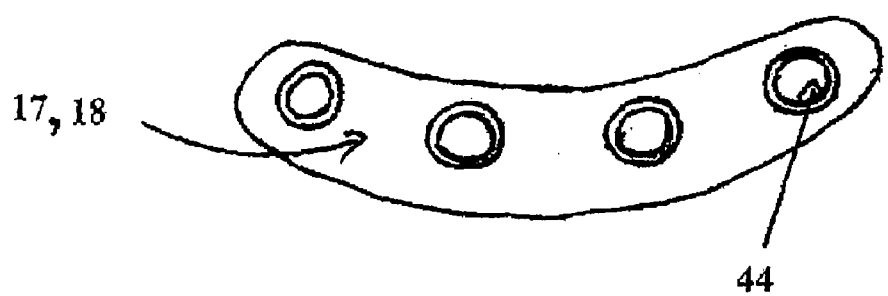
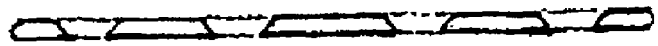
Fig. 10d

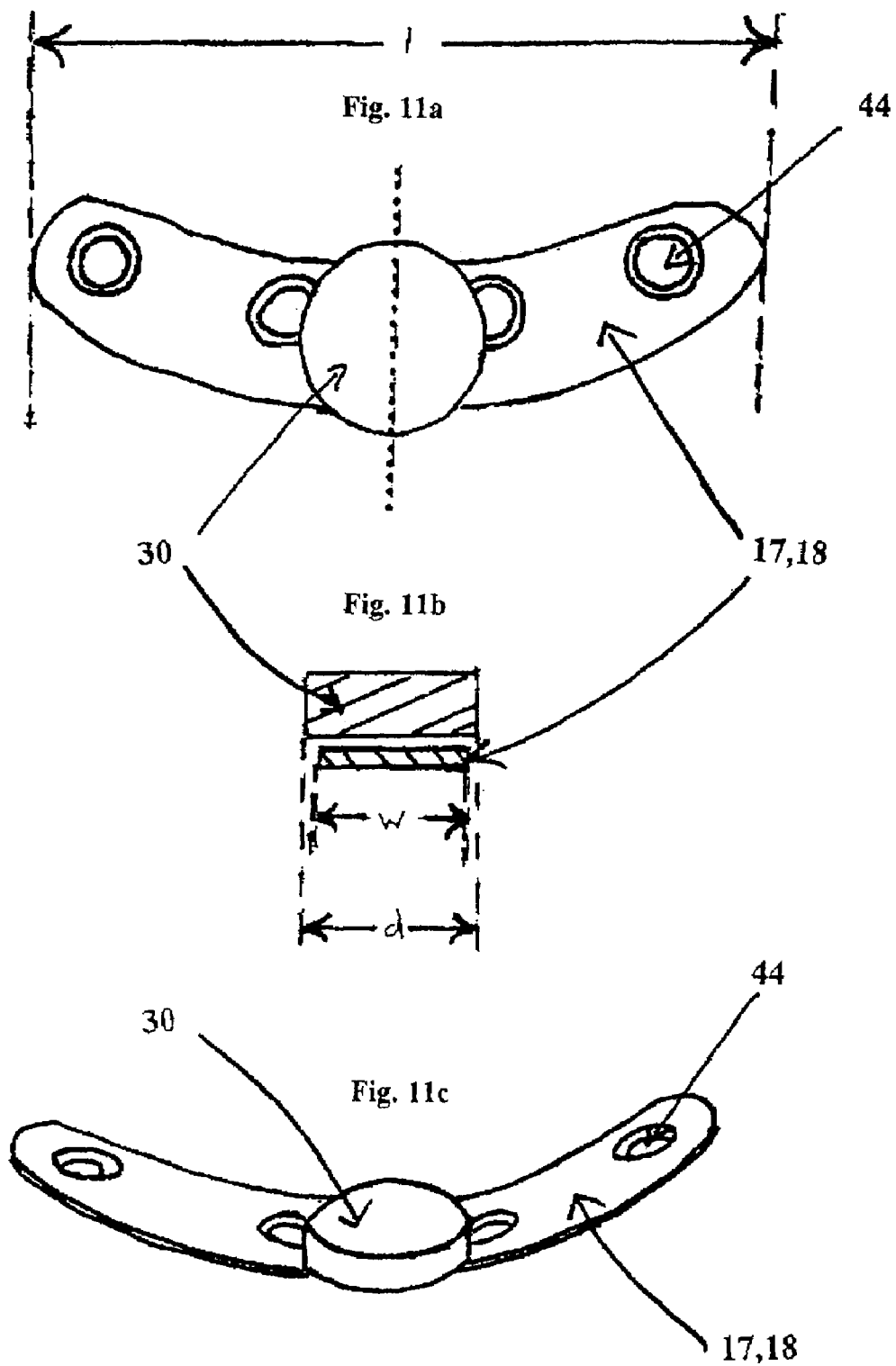

Fig. 13
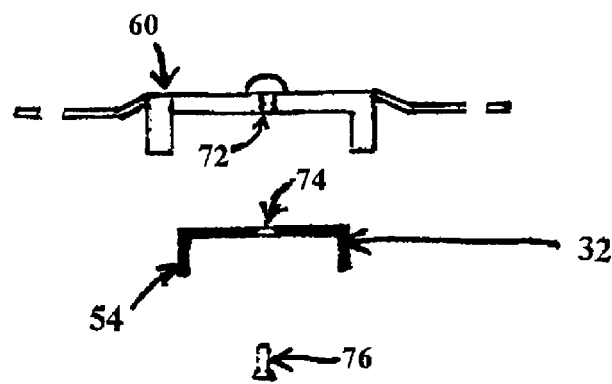
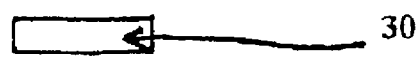
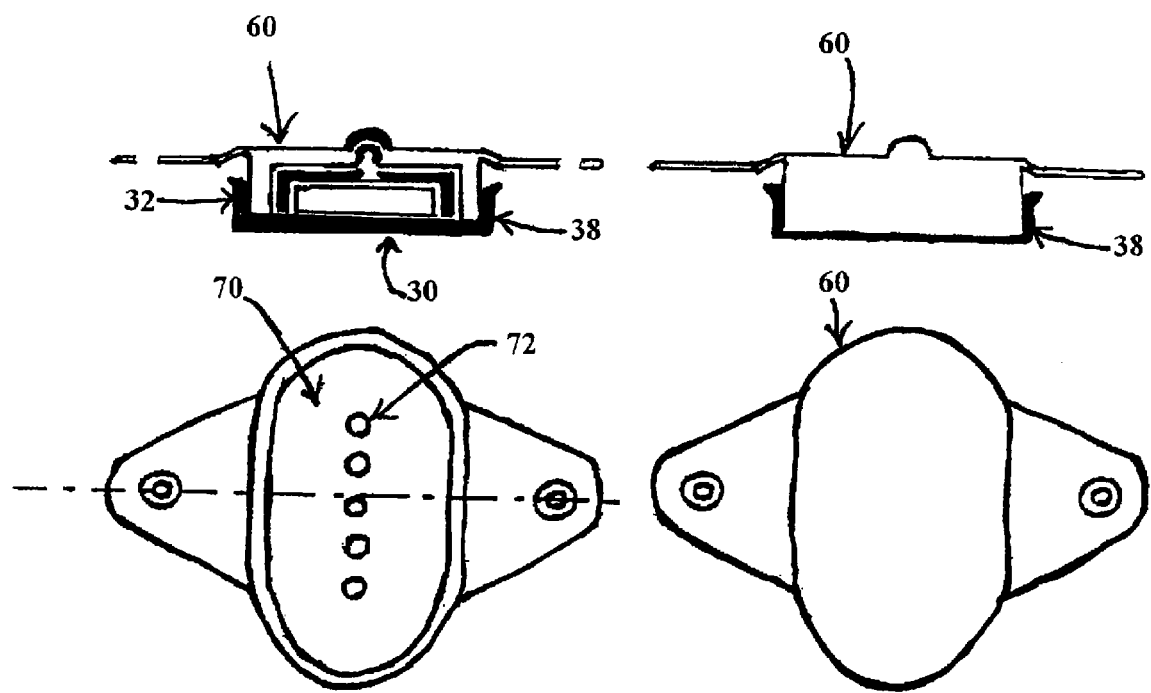

MAGNETIC DENTAL APPLIANCE

FIELD OF THE INVENTION

The present invention relates generally to medical devices. More particularly, the present invention relates to a magnetic dental appliance.

BACKGROUND OF THE INVENTION

Various fixed and removable dental appliances have been employed in dentistry and orthodontics over the years.

Removable dental appliances have been used to treat conditions such as snoring, sleep apnea, bruxism, myofascial pain, and pain and inflammation associated with temporomandibular joint (TMJ) dysfunction. While several prior art appliances have been shown to be effective, they typically lack comfort thereby negatively impacting patient compliance. Patient compliance is key in any patient-driven treatment, since lack of compliance renders the treatment ineffective.

The act of positioning an acrylic splint, or biteguard, over the teeth of the upper or lower dentition has been shown to relax tense musculature. This is accomplished by the splint preventing the existing occlusion (bite) from controlling the jaw-to-jaw relationship at maximum intercuspation (Dawson (1989). Evaluation, Diagnosis, and Treatment of Occlusal Problems ($2^{nd}$ Ed). Saint Louis, Mo.: Mosby, pg. 184-190). Because all corrective tooth inclines are separated, permissive splints, or de-programmers, allow the muscles to function according to their own coordinated interactions, thus eliminating the cause and the effects of muscle incoordination. Any splint design is permissive if it unlocks occlusal incline contacts and provides a smooth gliding surface that permits uninhibited muscle positioning of the mandible. Separation of the posterior teeth substantially reduces the contractile strength and activity of the elevator muscles. Thus, the loading pressure against the joints is lessened.

Advancing the mandible can relieve pain associated with some types of TMJ dysfunction, including extracapsular TMJ pain. It is very common for patients with TMJ pain and discomfort to hold their lower jaw forward during the day and, in doing so, the mandibular condyles do not impinge on the tender retrodiscal tissues (as in retrodiscitis) or the inflamed capsular ligament (as in capsulitis). However, this conscious positioning of the jaw is lost during sleep. A removable dental appliance for opening the bite and/or advancing the mandible slightly, worn during sleep, can be quite effective in relieving extracapsular TMJ pain.

Bruxism is a condition characterized by parafunctional clenching and grinding of the teeth which can occur during wake or sleep. Bruxism causes wear and breakdown of the teeth (dentition) and the subject is generally unaware of their destructive behavior. For patients who suffer from bruxism, providing a splint over the upper and/or lower teeth protects the occlusal surfaces of the teeth from destructive forces generated during bruxing. Advancing the mandible slightly, as well as providing occlusal (bite) contact on the anterior segment of the appliance lessens the amount of force that can be generated by the bruxing patient, since forces are reduced when the posterior teeth are not engaged. Advancing the mandible slightly after opening the bite can further reduce clenching forces. Reduction in grinding and clenching can also relieve muscle pain and reduce the frequency and severity of headaches associated with bruxism.

Headache sufferers diagnosed with TMJ syndrome are typically treated with a jaw-repositioning appliance, designed to relieve pressure on the distressed temporomandibular joint and to allow a proper jaw-to-skull relationship. Typical of these are the orthotics or splints described in U.S. Pat. Nos. 4,671,766 and 4,519,386. The appliance covers the upper and/or lower posterior teeth and dictates jaw position by guiding the opposing jaw into the "normal" position. Unfortunately, the posterior teeth of the upper and lower jaws are approximated by way of the appliance, thus allowing the full force of the clenching to persist.

U.S. Pat. No. 5,085,584 discloses an intraoral discluding device for the prevention of tension, migraine headaches and TMJ syndrome caused by chronic clenching of the posterior mandibular and maxillary teeth by the temporalis muscle. The discluder is a small intraoral device having a dome-shaped tab supported by a conventional palatal arch attachment member which is retained by bent orthodontic wire. The device is inserted in the mouth and retained against the upper anterior teeth with the tab extending such that, as the mouth is closed, the tab comes into contact with the lower anterior incisal edges before the posterior teeth can touch each other. This renders the temporalis muscles ineffective, preventing high pressure clenching of the posterior teeth. This device does not provide a means of advancing the mandible.

Although it is well known that advancing the mandible can relieve TMJ pain and reduce bruxing, the concept of advancing the mandible to open the airway, such as to treat apnea or snoring, is relatively new to the field of dentistry.

Apnea is generally defined as a cessation of breathing, or airflow, lasting 10 seconds or more. Hypopnea generally refers to a 50% reduction in airflow for 10 seconds or more. Sleep apnea is classified as central, obstructive, or mixed apnea. In central sleep apnea, the respiratory, or chest, muscles make no attempt to breathe as a result of a CNS disorder, resulting in a loss of oxygen to the lungs. In obstructive sleep apnea (OSA), the respiratory muscles attempt to inspire but a blockage in the upper airway prevents air from reaching the lungs. In mixed apnea, the patient presents with a combination of these problems. It should be noted that oral appliance therapy typically cannot address central or mixed sleep apnea.

Upper airway resistance syndrome (UARS) is characterized by loud snoring that causes frequent awakening. An UARS patient has all the symptoms of OSA but without the apneic or hypopneic events. Snoring is generally caused by a relaxing of the pharyngeal musculature leading to restriction of the airway, causing vibration of the surrounding tissue upon the passage of air. The tongue as well as the soft palate are believed to be major causative factors in both snoring and obstructive sleep apnea.

When a subject is positioned in the supine position, the tongue falls to the back of the throat and blocks the airway. Moving the mandible forward widens the airway, thereby preventing or reducing snoring.

Sleep apnea is associated with an increased risk of hypertension and other cardiovascular and cerebrovascular diseases. Advancing the mandible has been shown to draw the tongue out of the airway, thereby opening the airway, to reduce episodes of snoring and obstructive sleep apnea. A recent epidemiological study of the general population reported that sleep breathing disorders, especially obstructive sleep apnea syndrome, are more prevalent in populations with tooth grinding (3.4 to 4.8%) than in those without (1.4%) (Kato et al. Bruxism and Orofacial Movements During Sleep. In, Attanasio and Bailey (eds.). Sleep Disorders: Dentistry's Role. Dental Clinics of North America, 45(4), 2001, p. 658). Severe occlusal wear (more than 20% of the clinical crowns) may indicate severe bruxism and complicate oral appliance therapy (Lowe. Oral Appliances for Sleep Breathing Disorders. In, Kryger, Roth and Dement (eds). Principles and Practice of Sleep Medicine ($3^{rd}$ Ed.). Philadelphia, Pa.: Saunders, 2001, pp. 930).

Various appliances for advancing the mandible have been developed over the years. Most of the two-piece appliances on the market today, i.e. appliances having both an upper and lower arch attachment member, serve to fix a patients jaw in the forward position during sleep. However, pain and discomfort result when the jaw is restricted from movement for extended periods of time. Many known two-piece appliances do not allow sufficient translational or sagittal jaw movement while the appliance is in place. Many also restrict vertical jaw movement. Discomfort reduces patient compliance, thereby reducing the overall effectiveness of the patient-driven treatment. Since patient compliance increases with the comfort and ease of using a dental appliance, there is a need to develop more comfortable dental appliances.

U.S. Pat. No. 5,427,117 discloses a dental device for preventing snoring and improving breathing, which includes an upper and lower arch attachment member of a deformable material in which a mold of the subject's upper and lower teeth is formed. A post extends from the upper arch attachment member and contacts the lower arch attachment member so that the lower jaw is extended forward, thereby reducing snoring. The device is designed to permit some movement of the lower jaw for improved comfort. In a particular embodiment, the forward location of the post, with respect to the user, is adjustable to allow titration of the degree of mandibular advancement. In a preferred embodiment, the upper and lower jaws are "locked" such that they cannot be opened more than a predetermined amount. Translational or lateral jaw movements are restricted as well. U.S. Pat. Nos. 5,365,945, 5,566,683, 6,305,376 and 6,845,774 describe similar devices.

In an attempt to offer improved comfort to the patient, a device called the SILENSOR™ snoreguard was developed, which creates tension between upper and lower arches to advance the mandible. The device consists of two transparent arch attachment members, or splints, one each for the upper and lower jaw. The lower jaw is held in a predetermined position by two connectors that are fixed laterally to the arch attachment members. The connector members are oriented in such a manner as to draw the jaw forward. The device permits limited movement of the lower jaw since the connector members offer a somewhat elastic property.

The above-mentioned appliances all require rigid mechanical components (i.e. hooks, wires, plastic fasteners, etc.) in order to produce advancement of the mandible. Mechanical components are subject to wear and destruction and can render an appliance bulky and cumbersome for a patient to wear. Furthermore, locking fasteners can snag the soft tissue in the oral cavity, including the tongue, causing discomfort and even lesions.

A magnetic dental appliance for treatment of snoring and sleep apnea was recently developed and studied in Sweden (Bernhold et al., *Am J Orthod Dentofacial Orthop* 1998; 113, 144-55). This device incorporates 8 magnets (2 in each posterior quadrant) in an "open field" configuration to advance the mandible. The magnets are embedded in an upper and lower acrylic arch attachment member in the posterior segment of each member. The magnets are positioned in both members such that the north poles of the magnets in one member attract the south poles of the magnets in the opposing member to urge the mandible forward. Strong magnetic attraction between the upper and lower sets of magnets essentially prevents jaw movement, which causes significant discomfort to the patient since the jaw muscles and TMJ are held in the same position for extended periods. The appliance is not titratable so no adjustability is permitted once the appliance is cast.

The use of magnets in the oral cavity is not an entirely new concept. Magnets have been used to fasten dentures to implant fixtures for a number of years now. The original systems employed the attractive forces between coated Alnico V magnets, implanted in the mandible, and magnets embedded in the dentures. These original systems met with little success due to insufficient holding power. Since the introduction of rare earth magnets in the 1970's to 1980's, such as samarium-cobalt and neodymium-iron-boron magnets, it has become possible to produce magnets with small enough dimensions for dental applications and yet still provide the necessary forces.

The first magnetic denture attachment devices were of the "open field" type, wherein two unshielded magnets are placed in the oral cavity in force-coupled relationship. Due to concerns about the possible harmful effects of "open field" magnetic forces on the local tissues, most magnetic denture systems are now of the "closed field" type. In this type of system, a soft magnetic or ferromagnetic material, such as ferritic or martensitic stainless steel or Pd—Co—Ni alloy, is implanted into the jaw, rather than a magnet, to provide attractive force to hold the denture in place. This implant is known as a "keeper". In this configuration, the magnetic field lines are shunted through the keeper as it is the path of minimum energy and there is no magnetic field experienced in the oral cavity.

U.S. Pat. Nos. 6,659,771, 5,678,998, 5,013,243 and 6,299,450 describe small yet powerful magnets for cooperating with a non-magnet implanted "keeper" for denture attachment. The non-magnet keeper is made of a magnet-attracted material, such as a soft magnetic or ferromagnetic material, but is not a permanent magnet.

Magnets have been employed in aspects of orthodontics and dentistry other than denture attachments. U.S. Pat. No. 4,396,373 describes a removable orthodontic appliance for intruding one or more teeth. The appliance includes two rigid caps having internal shapes conforming to the crown portions of juxtaposed molars in the maxilla and mandible, respectively. The caps are adapted to be removably secured to said teeth. Two permanent magnets carried by the two caps, respectively, having facing poles which are in registry when the mouth is normally closed, exert a magnetic force in a direction substantially normal to the occlusal plane. The opposing magnets have confronting poles with like-polarity such that the magnets repel and develop intrusive forces upon the respective teeth.

U.S. Pat. No. 4,671,767 discloses both fixed and removable orthodontic devices that use magnets to correct Class II malocclusions. The magnets are secured to removable or fixed orthodontic devices and are positioned bilaterally in the posterior molar regions. The faces of the magnets are oriented such that they repel each other, thereby creating magnetic forces parallel to the occlusal plane for urging the mandible forward. Correction of Class II malocclusions involves, among other things, acting upon the mandible to urge it anteriorly until the jaw muscles adapt and, if possible, until regrowth of the condyle into the glenoid fossa occurs. Alignment of the teeth may be corrected in the process.

The magnetic orthodontic devices described above employ "open field" magnetic configurations, which are potentially harmful to the local tissues in the oral cavity, especially since the devices are designed for long-term use. Furthermore, the appliances are uncomfortable to wear.

Biological safety testing of magnets containing rare earth elements has evaluated both the effects of the static magnetic field and possible toxic effects of the materials or their corrosion products. These studies have demonstrated negligible cytotoxic effects of the magnetic field. However, it is of paramount importance to prevent corrosion from occurring. A clinical, histological, and immunohistochemical study, found no adverse long term effects on human buccal mucosa which had been in contact with acrylic-coated neodymium iron boron magnets and subject to the static magnetic field (Bondmark et al. Long-term effects of orthodontic magnets on human buccal mucosa: a clinical, histological and immunohistochemical study. *European Journal of Orthodontics* 1998; 20, 211-218). The evidence currently available from biological safety testing would suggest that the risk of harmful biological effects are negligible (Noar and Evans. Rare Earth Magnets in Orthodontics: An Overview. *British Journal of Orthodontics* 1999; 26(1), 29-37).

A subgroup of patients using oral appliance therapy, particularly those who suffer from sleep bruxism, experience considerable jaw discomfort the morning after wearing a rigid, single jaw position, oral appliance. A need to develop oral appliances that could allow for lateral jaw movement, as well as some degree of vertical jaw opening, was identified (Lowe. Oral Appliances for Sleep Breathing Disorders. Kryger, Roth and Dement (eds). Principles and Practice of Sleep Medicine ($3^{rd}$ Ed.). Philadelphia, Pa.: W B Saunders, 2001, pp 931).

It is desirable to provide an improved removable dental appliance for treatment of conditions such as snoring, obstructive sleep apnea, bruxism, myofascial pain and TMJ syndrome, that is simple and durable in construction and, most importantly, comfortable and safe for the patient. Comfort is an important factor in any patient-directed treatment where compliance is key.

SUMMARY OF THE INVENTION

It is an object of the present invention to obviate or mitigate at least one disadvantage of known oral dental appliances.

The present invention generally provides a magnetic dental appliance. The dental appliance of the invention is suitable for opening the bite and/or advancing the mandible of a patient in need thereof. The magnetic dental appliance can be used in the treatment of various conditions, including but not limited to, snoring, obstructive sleep apnea, bruxism, headaches, some TMJ problems and myofascial pain dysfunction syndrome.

In a first aspect, the present invention provides a magnetic dental appliance that is more comfortable to wear than known appliances. The appliance uses magnetic force to selectively position the mandible while still permitting movement of the mandible relative to the maxilla.

In another aspect, the magnetic dental appliance is used to advance the mandible relative to the maxilla. For advancing the mandible, the appliance uses magnetic force to gently draw the mandible forward. Magnetic mandibular advancement may optionally be augmented by class II elastomeric traction between upper and lower arch attachment members, especially where the degree of advancement required is greater than several millimeters.

The magnetic dental appliance of the present invention is unique in that it allows: antero-posterior (ie. protrusive-retrusive or sagittal) jaw movements against magnetic forces, optionally combined with elastomeric forces; lateral translational movement against the resistance of magnetic forces, optionally combined with elastomeric forces; and vertical opening against an initial resistance to opening by the magnetic forces, optionally combined with elastomeric forces. The optional elastomeric forces allow opening of the jaws but increasingly resist it as the jaws are further separated.

The magnetic dental appliance comprises an upper and lower arch attachment member for removably securing the appliance to at least a portion of the dentition, preferably the entire upper and lower dentition. Magnetic force is created between a magnetic component, positioned anteriorly on a first arch attachment member, and a magnet-attracted element, positioned on a second arch attachment member for engagement with the magnetic component.

In one embodiment, the removable magnetic dental appliance comprises an upper arch attachment member for removably engaging at least a portion of the upper dentition and a lower arch attachment member for removably engaging at least a portion of the lower dentition. A magnetic component is positioned anteriorly on one of the upper arch attachment member or the lower arch attachment member and a magnet-attracted element is provided on the other of the upper or lower arch attachment member for magnetic engagement with the magnetic component when the upper and lower arch attachment members are substantially vertically aligned.

The magnetic dental appliance is shaped and constructed to permit translational or sagittal movement of the upper arch attachment member relative to the lower arch attachment member when the magnetic component and the magnet-attracted element are magnetically engaged. Movement of the upper arch attachment member relative to the lower arch attachment member is permitted by sliding the magnetic component along the magnet-attracted element.

In a preferred embodiment, the magnetic component is on the upper arch attachment member and the magnet-attracted element is on the lower arch attachment member.

A patient is able to move the mandible relative to the maxilla while wearing the magnetic dental appliance, making the appliance of the invention more comfortable than known appliances during extended wear. Increased comfort results in increased patient compliance.

In a further aspect, there is provided a removable magnetic dental appliance for advancing the mandible, which permits translational and sagittal movement of the mandible during wear for improved comfort to a patient, thereby increasing patient compliance. Furthermore, a wearer of the appliance is able to move the mandible vertically by simply opening the jaws with sufficient force to overcome the magnetic force. This feature not only offers a patient improved comfort but also provides a safe alternative to dental appliances that "lock" the jaws against vertical movement, since a patient can quickly open the jaws in case of emergency (i.e. vomiting or severe apneic episode), even if the patient is asleep or in a panicked state.

In certain cases, elastomeric modules, known in the art, are attached to the magnetic dental appliance to aid in urging the mandible forward.

In a further aspect, the present invention provides a use of the removable magnetic dental appliance of the invention for the treatment or prevention of snoring, sleep apnea, some forms of temporomandibular joint pain or inflammation, myofascial pain or bruxism.

In another aspect of the invention, there is provided a kit comprising the magnetic dental appliance of the invention, in assembled or unassembled form, together with instructions for use in the treatment of snoring, sleep apnea, some forms of temporomandibular joint pain or inflammation, myofascial pain or bruxism.

In another aspect, the present invention provides a magnetic dental appliance that is safer to wear than known removable magnetic appliances since the appliance employs a "closed field" magnetic configuration, such that magnetic fields are not experienced in the oral cavity.

"Advancement" or "advancing" refers to positioning of the mandible in a forward or anterior position relative to the maxilla, when compared to the natural position of the mandible relative to the maxilla at rest.

"Titration" can be defined as the gradual forward movement of the mandible relative to the maxilla. A titratable dental appliance is one that allows for adjustment of the relative mutual positioning of the mandible relative to the maxilla when the appliance is in place, without the need to entirely reconstruct a new appliance.

With respect to jaw movement, the term "translational" refers to lateral or side-to-side movements of the mandible relative to the maxilla; "sagittal" refers to anterior-posterior movement of the mandible relative to the maxilla; and "vertical" refers to up-down or open-closed movements of the mandible relative to the maxilla.

"Subject", as used herein, refers to an individual who suffers from a condition, including but not limited to, snoring, sleep apnea, temporomandibular joint dysfunction, myofascial pain or bruxism, or who would otherwise benefit from use of the magnetic dental appliance of the invention. The term "patient" is used synonymously with "subject" herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 4 is a lateral view of the appliance of FIG. 1 in place on the dentition of a wearer, wherein FIG. 4a) shows the mandible in a retruded position without the magnetic component engaged, FIG. 4b) shows the mandible in a protruded position with magnetic component engaged and FIG. 4c) shows the mandible in a protruded position with magnetic component engaged and optional elastomeric modules in place;

FIG. 6 shows anterior views of the dental appliance of FIG. 1 wherein FIG. 6a) shows the appliance without magnetic component engaged (i.e. jaws open), FIG. 6b) shows the appliance without magnetic component engaged with elastomeric modules in place, FIG. 6c) shows the appliance with magnetic component engaged (i.e. jaws closed) and FIG. 6d) shows the appliance with magnetic component engaged and with elastomeric modules in place;

FIG. 9 shows five perspective views of the magnet-attracted element embodied in FIGS. 2 and 3;

FIG. 11 illustrates the tendency for the magnet to center itself on the magnet-attracted element, wherein FIG. 11a) is a superior view, FIG. 11b) is a sectional view and FIG. 11c) is a superior oblique view;

FIG. 13 illustrates a titratable serial screw mechanism; and

DETAILED DESCRIPTION

Generally, the present invention provides a magnetic dental appliance suitable for altering the relative mutual positioning of the jaws, and in a preferred embodiment, for advancing the mandible of a subject in need thereof. Altering the position and bite of the jaw is known to provide relief to patients suffering from TMJ pain and inflammation, myofascial pain, headaches and bruxism. Mandibular advancement is known to provide relief to patients suffering from various conditions including, but not limited to, snoring, obstructive sleep apnea, TMJ pain and inflammation, myofascial pain, headaches and bruxism.

Additional uses of the magnetic dental appliance of the present invention are the concomitant treatment of bruxism with the treatment of snoring and obstructive sleep apnea, where required. The treatment of myofascial pain dysfunction syndrome (MPDS) as well as extracapsular TMJ problems, such as retrodiscitis and capsulitis, can also be accomplished with this device. If the Anterior Bite Plane causes increased discomfort, this indicates that an intracapsular problem may exist (Dawson (1989). Evaluation, Diagnosis, and Treatment of Occlusal Problems ($2^{nd}$ Ed). Saint Louis, Mo.: Mosby, pg. 199). This could be a contra-indication for the use of the magnetic dental appliance of the invention.

Dentists realized early on that determining the correct jaw position was the most difficult step in using oral appliances successfully. Considerable variations in the initial comfort range of the antero-posterior movement of the mandible, and differences in the speed and amount of forward jaw position that any given patient could tolerate were found. Single jaw position or non-adjustable appliances often need to be remade if the initial jaw position proves to be inadequate. Gradual titration forward of the mandible without the necessity of making a new appliance each time thus became an important objective and adjustable appliances were invented and marketed (Lowe. Oral Appliances for Sleep Breathing Disorders. Kryger, Roth and Dement (Eds). Principles and Practice of Sleep Medicine ($3^{rd}$ ed.). Philadelphia, Pa.: W B Saunders, 2001, pp. 931).

With either fixed or adjustable appliances, the initial position of the mandible is generally about 60% to about 80%, preferably about 70% to about 75%, of maximum protrusion relative to maximum retrusion (Ivanhoe and Attanasio. Sleep Disorders and Oral Appliances. In, Dental Clinics of North America: Sleep Disorders: Dentistry's Role, Eds. Attanasio and Bailey, vol. 45(4), October 2001, pp. 749). The incisors are generally vertically separated by between about 5 and about 7 mm. If, as frequently happens, successful results are achieved, titration is not necessary. If titration is required to successfully treat the sleep disorder, the mandible is slowly protruded, often in increments of about 0.25 mm per night. This anterior movement is continued until satisfactory results are achieved.

Figure 1A:
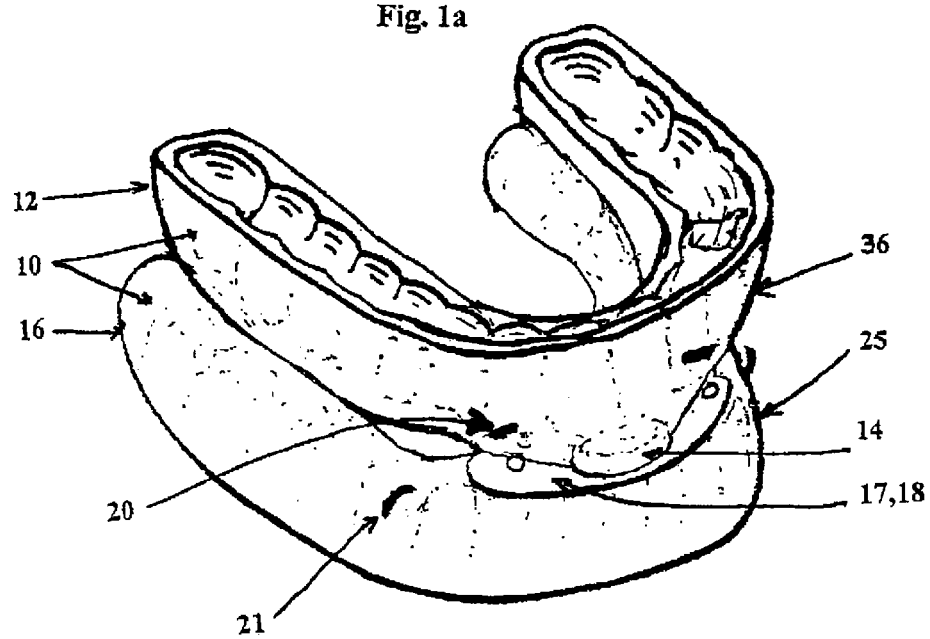
FIG. 1 is a perspective view of a magnetic dental appliance in accordance with an embodiment of the invention wherein FIG. 1a) shows the appliance without elastomeric modules and FIG. 1b) shows the appliance with optional elastomeric modules in place.
Figure 1B:
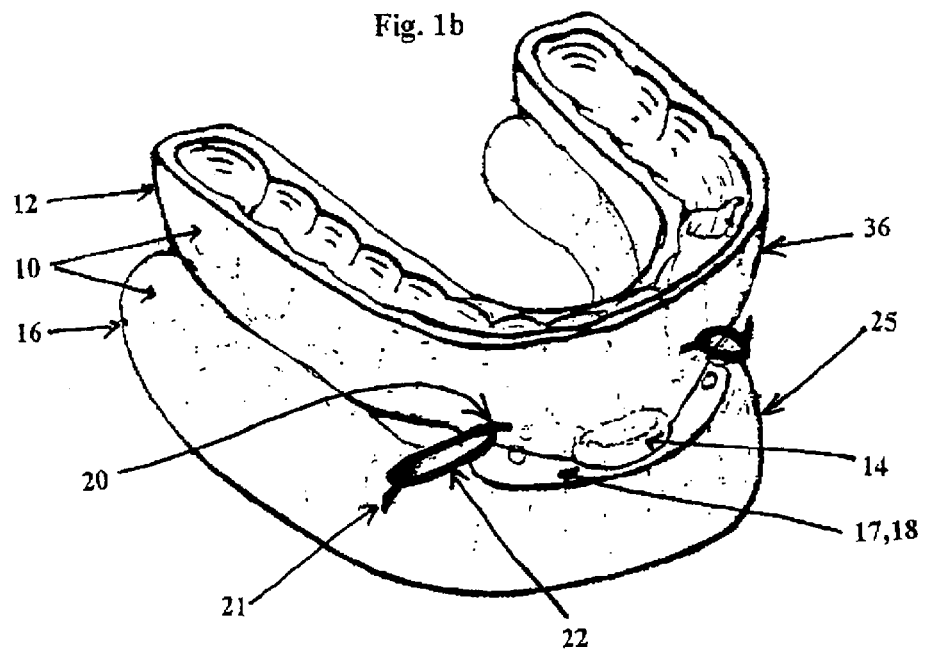

As shown in the embodiment of FIG. 1, the magnetic dental appliance (10) of the invention comprises an upper arch attachment member (12) and a lower arch attachment member (16), the construction and function of which is discussed in more detail below. In the exemplified embodiment, a magnetic component (14) is positioned anteriorly on the upper arch attachment member (12) and a magnet-attracted element (18) is positioned on the lower arch attachment member (16). The magnet-attracted element (18) is positioned opposite the magnetic component (14) for magnetic engagement with the magnetic component (14) when the appliance is worn by a subject.

Figure 2:
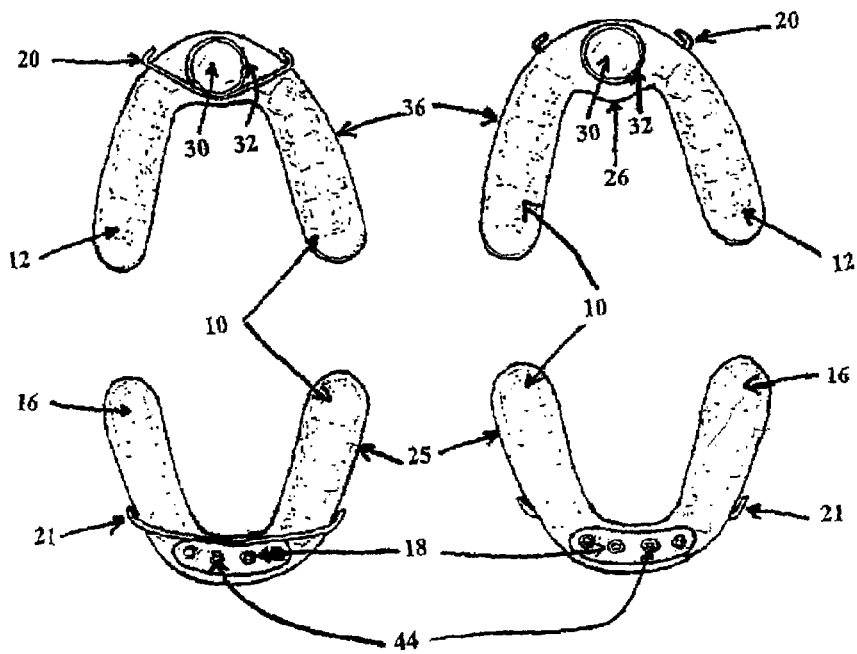
FIG. 2 is a bottom plan view of the dental appliance of FIG. 1 at two stages during production wherein FIG. 2a) shows the magnetic components and optional bilateral elastic hooks exposed on the surface of the arch attachment members and FIG. 2b) shows the various components covered with cold cure methyl methacrylate resin.
Figure 3:
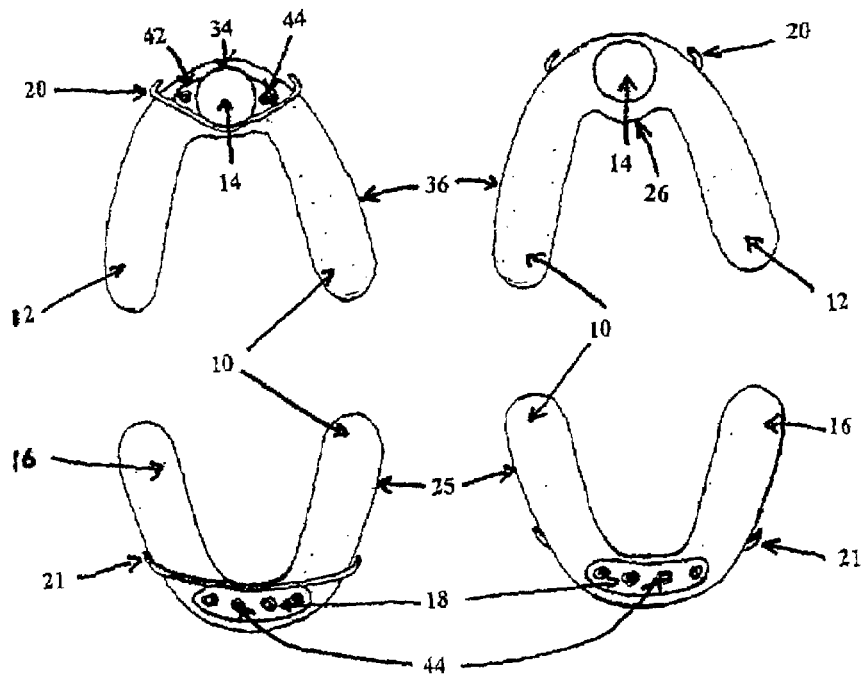
FIG. 3 is a bottom plan view of the a dental appliance in accordance with another embodiment of the invention at two stages during production, wherein FIG. 3a) shows the magnetic components, including a non-magnetic sleeve covering the magnet, and optional bilateral elastic hooks exposed on the surface of the arch attachment members and FIG. 3b) shows the various components covered with cold cure methyl methacrylate resin.
Figure 7:
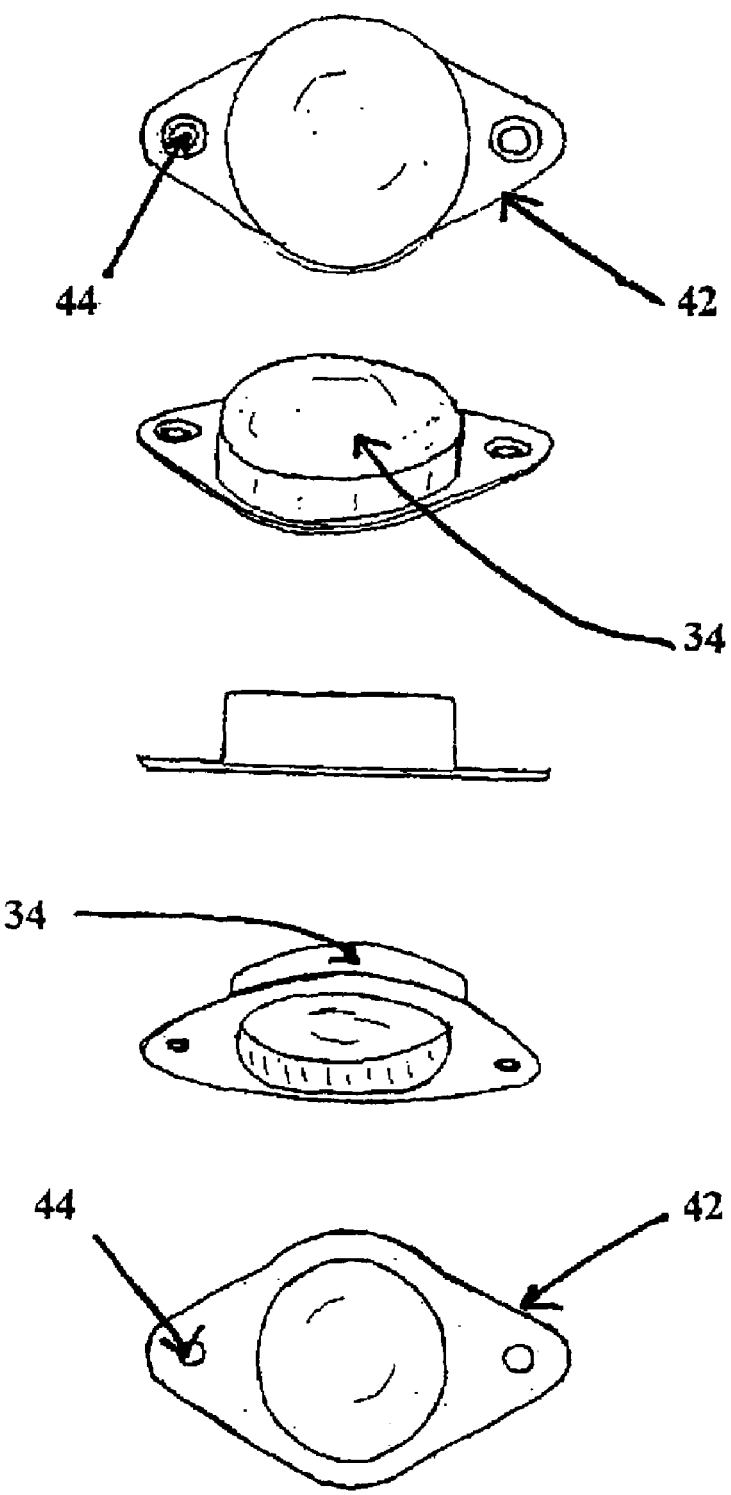
FIG. 7 shows five perspective views of an embodiment of a corrosion resistant sleeve, in accordance with an aspect of the present invention.
Figure 8:
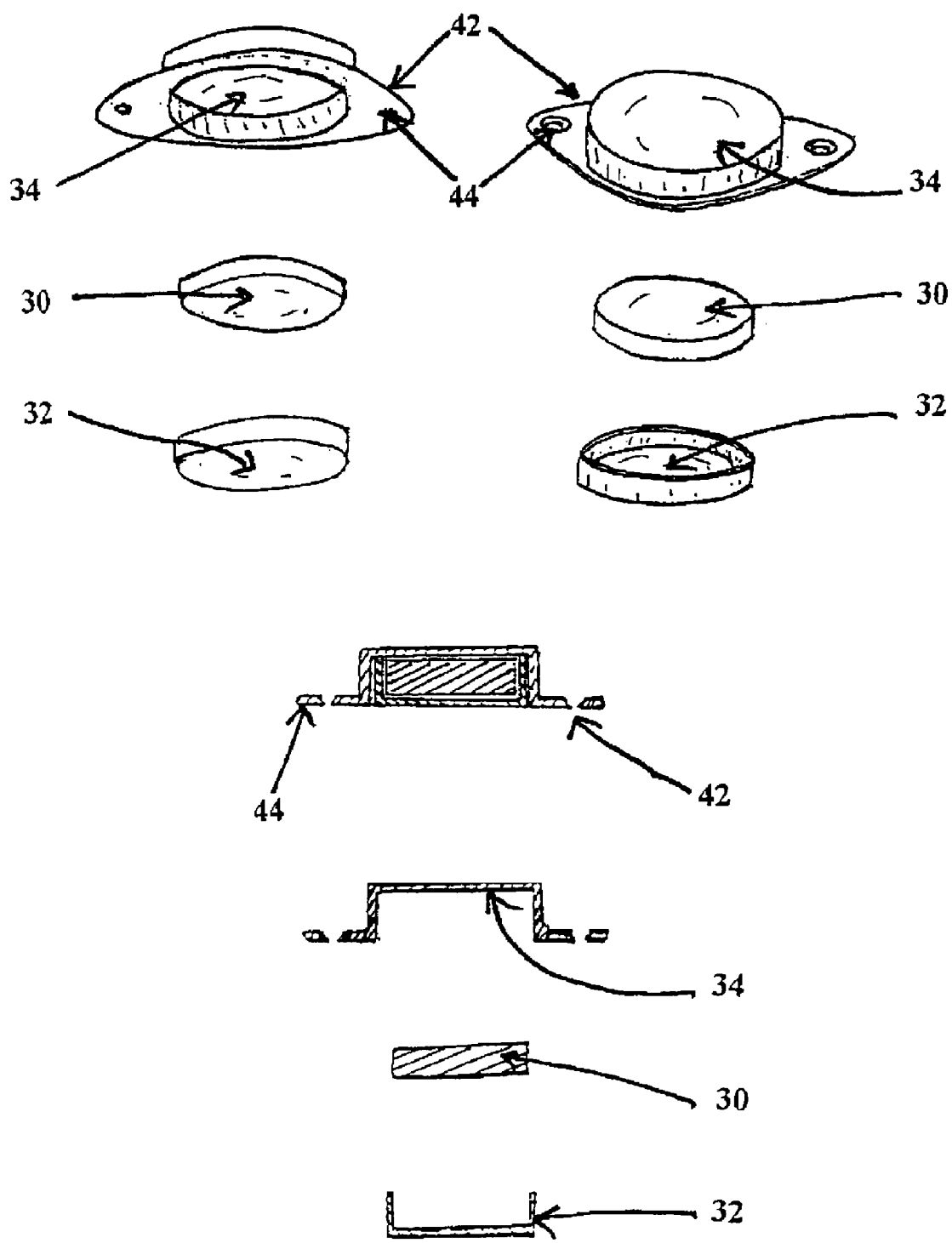
FIG. 8 shows two exploded perspective views and an exploded cross-section of the magnetic component embodied in FIG. 3a), showing a magnet, a ferromagnetic cup and a corrosion resistant winged sleeve.

The magnetic component includes a magnet (30) and may also include other components, such as a magnet cup, or ferromagnetic cup (32), and/or a retentive sleeve (34). FIGS. 2 and 3 illustrate two embodiments of a dental appliance (10) in accordance with the present invention. In FIG. 2, the magnetic component comprises a magnet (30) in a ferromagnetic cup (32). In the embodiment shown in FIG. 3, the magnet and ferromagnetic cup are covered by a corrosion resistant retentive sleeve (34). FIG. 7 shows the retentive sleeve (34) of FIG. 3 from different perspective views and FIG. 8 shows the magnetic component (14) of FIG. 3 in exploded views. The sleeve (34) exemplified in the figures has two retentive wings (42), each with retentive holes (44) for attaching the magnetic component (14) to the upper arch attachment member (12).

In the embodiments shown in FIGS. 2 and 3, a first bilateral hook (20) is fixed to the upper arch attachment member (12) and a second bilateral hook (21) is fixed to the lower arch attachment member (16). The bilateral hooks (20 and 21) are for attaching elastomeric modules to the appliance and may be formed from stainless steel orthodontic wire or any other suitable material. Although each bilateral elastic hook is exemplified as a continuous piece of wire, a skilled person will appreciate that the hook need not be continuous. Individual hooks or studs could be fixed laterally to the appliance for attaching the elastics. The bilateral elastic hooks (20, 21) may be fixed to the arch attachment members directly, for example, by adhesion or by embedment in the material of the arch attachment member, or indirectly. FIGS. 2a and 3a show the magnetic component (14), the magnet-attracted element (18) and the bilateral elastic hooks (20, 21) exposed on the arch attachment members (12, 16), while FIGS. 2b and 3b show all components fixed to the arches and covered with cold cured methyl methacrylate resin. Typically, the upper bilateral elastic hook (20) and lower bilateral elastic hook (21) are separated from one another by about 5 mm to about 10 mm when the magnetic component (14) and magnet-attracted element (18) are engaged, as can be seen in FIG. 1. Preferably, the hooks are separated by about 7 mm. The initial elastic module (22) used preferably has a diameter of about 7 mm. In this arrangement, the elastic module (22) initially used would have a force close to zero since the inside diameter (or length) of the elastic module (22) is preferably about 7 mm. When a smaller elastic module (i.e. 6 mm diameter) is used, then the lower arch attachment member (16) will be held more tightly against the upper arch attachment member (12) and in a more anterior or protruded position. If a lighter elastic module is used (i.e. 8 mm diameter), the lower arch attachment member (16) will be held more loosely against the upper arch attachment member (12), which would allow the mandible to move to a more posterior or retruded position when the magnetic component (14) and magnet-attracted element (18) are not engaged. It is preferable for the upper (20) and lower (21) bi-lateral elastic hooks be as close to the superior surface of the arch attachment members as possible. In this configuration the elastic forces are primarily sagittal rather than vertical when the magnetic component (14) and the magnet attracted element (18) are engaged.

If no elastic traction is used, then the lower arch attachment member (16) would be free to move to the fully retruded position when the magnetic component (14) and magnet-attracted element (18) are not engaged. The patient may begin wearing the appliance with no elastic traction to become familiar with the proposed treatment position by protruding the mandible and engaging the magnetic component (14) with the magnet-attracted element (18). This would be followed by applying progressively stronger elastic modules (22) over time until the desired result is attained. If the cessation of snoring or obstructive sleep apnea has not been attained when the strongest elastic module is reached, then the initial position of the magnetic component (14) or magnetic-attracted element (18) can be adjusted. This can be done by either repositioning the magnetic component (14), typically anteriorly, on the upper arch attachment member (12) or repositioning the magnet-attracted element (18), typically posteriorly, on the lower arch attachment member (16), or both.

Figure 5A:
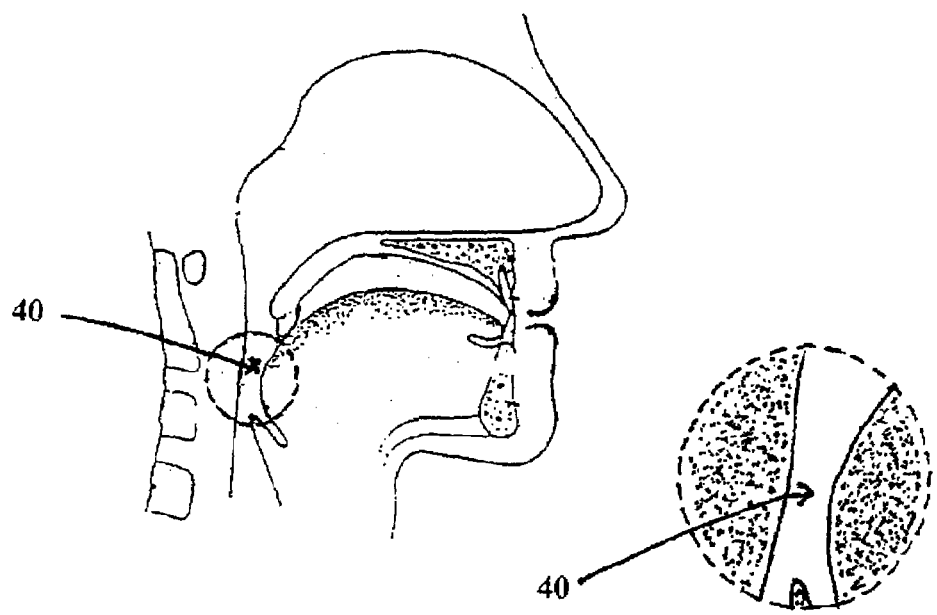
FIG. 5 is a lateral view of a saggital section through the head wherein FIG. 5a) shows the airway narrowed when no appliance is in place and FIG. 5b) shows opening of the airway when the appliance is in place with magnetic component engaged and optional elastomeric modules in place.
Figure 5B:
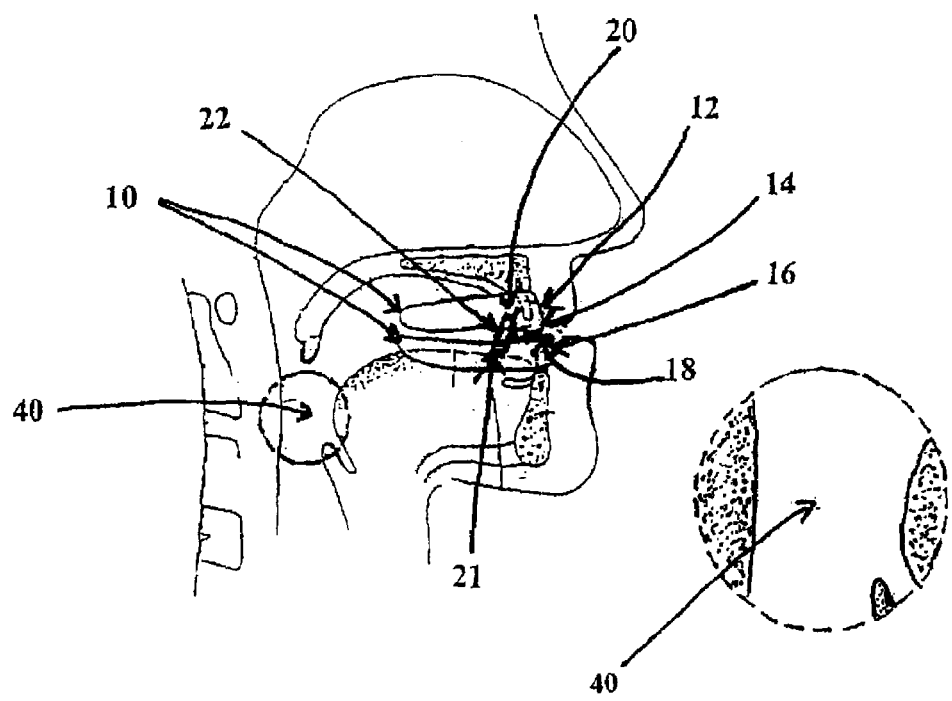

FIG. 4a illustrates the positioning of the magnetic dental appliance over the dentition of a subject. FIG. 4b illustrates the advancement of the mandible when the magnetic component (14) and magnet-attracted element (18) are engaged and FIG. 4c illustrates the combined use of elastic traction. FIG. 5 illustrates the opening of the airway (40) when the mandible is advanced using the magnetic dental appliance (10) of the invention in combination with elastic traction.

Arch Attachment Member

An arch attachment member refers to a member having means for attaching the dental appliance to at least a portion of the dentition or gum, preferably to the entire upper and lower dentition, as illustrated in FIG. 4. Any means known in the art for attaching a dental appliance to all or a portion of the dentition may be employed, for example, dental arches or dental wires. A preferred arch attachment member is a dental arch or splint. A dental arch is a standard or custom-fitted splint that fits over the upper or lower dentition, preferably over the entire upper or lower dentition. A preferred embodiment of the invention, as shown in FIG. 1, makes use of custom-fitted upper and lower arch attachment members (12 and 16, respectively) in the form of dental arches that fit securely to the unique dentition of a given subject. While standard-fit arch attachment members could also be used, they do not offer the security or comfort of a custom-fitted arch attachment member. Heat moldable arch attachment members can also be employed wherein a patient can mold the arches to the shape of the dentition using heat. For instance, a patient can purchase a kit comprising a heat-moldable dental appliance, in accordance with the present invention, together with instructions for use.

The arch attachment members (12, 16) can be formed from any suitable material known to those of skill in the art. For instance, an acrylic or elastomeric material can be used. A thermoactive acrylic can also be used.

Custom-fitted arch attachment members (12, 16) are preferably made of a pressure moulding material, an example of which is DURASOFT™ (Scheu Dental), which provides both a hard polycarbonate (PC 1.1 mm) or co-polyester base material and a soft polyurethane (PU 1.4 mm) material for a total thickness of about 2.5 mm. Where retention is a problem, the arch attachment members (12, 16) can be made with injection moulded thermoactive acrylic resin. Custom-fitted arch attachment members (12, 16) are generally designed for friction fit with the dentition.

The components, i.e. the magnetic component (14) and the magnet-attracted element (18), may be attached to the arch attachment members (12, 16) by any suitable means known in the art. Preferably, the components are attached using cold cure methyl methacrylate resin. The distal portions of the arch attachment members are relieved if necessary so that they do not contact either in centric occlusion or lateral and protrusive excursions. Preferably, the only contact allowed between the arch attachment members (12, 16) is on the anterior portion of the appliance, as illustrated in FIGS. 4*b*, 4*c* and 6*c*, 6*d*. for example.

FIG. 2 shows a preferred embodiment of the magnetic dental appliance at two stages during production, wherein FIG. 2*a* shows the components (14, 18) and optional bilateral elastic hooks (20, 21) exposed on the surface of the arch attachment members (12,

16) and FIG. 2*b* shows the components covered with cold cure methyl methacrylate resin. FIG. 3 shows an alternate preferred embodiment of the magnetic dental appliance at two stages during production. It is preferred that, initially, only the retentive holes (44) in the lower and/or upper components are used to affix the components to the arch attachment members (12, 16).

If it is necessary to reposition either the magnetic component (14) or the magnet-attracted element (18), the retentive resin can be drilled out of the retentive holes (44) and the component(s) can be removed. Preferably, the arch attachment members (12, 16) are returned to a semi-adjustable articulator in order to relocate the components. Alternatively, the components can be repositioned directly in the mouth. Usually, the upper magnetic component (14) would be positioned further labially but on occasion it will be more appropriate to reposition the magnet-attracted element (18) further lingually. This is a unique feature of the present appliance, since other titratable appliances allow for repositioning of the upper component only. Once the ideal position has been confirmed, for example, by trial wear, the magnetic component (14) and magnet-attracted element (18) are more securely embedded in or on the appliance by the sprinkle-on method of application for cold cure methyl methacrylate. Preferably, only the occlusal portion of the components are left exposed, as exemplified in FIGS. 2*b* and 3*b*.

As shown in the embodiments in FIGS. 2*b* (upper) and 3*b* (upper), a platform (26) is provided lingual to the magnetic component (14) on the upper arch attachment member (12) such that the lower arch attachment member (16) cannot be easily placed behind the platform (26), thus providing a free gliding motion from centric occlusion position to the desired protruded location.

Magnet

In recent years, permanent magnets have been employed in various medical devices for use in the living body, including the oral cavity. For use in a living body, safety of the magnetic material is important. Demonstration of a strong magnetic force in as small a volume as possible is also important in order to avoid burdening of the body and to permit use in restricted spaces.

There are several types of permanent magnets, including ferrite, alnico, ceramic and rare earth magnets. A rare earth magnet is a strong permanent magnet made from alloys of rare earth elements, or lanthanide and actinide metals, with other metals. They are substantially stronger than ferrite or alnico magnets. The magnetic field produced by rare earth magnets can be well over 1.2 teslas. By comparison, ferrite or ceramic magnets typically exhibit around 50 to 100 milliteslas. The most powerful and affordable type of rare earth magnet is a neodymium magnet. Neodymium magnets are made of neodymium, iron, and boron in the general formula $Nd_2Fe_{14}B$.

A rare earth magnet can be easily oxidized due to poor corrosion resistance. The use of a rare earth magnet in the oral cavity must therefore be accompanied by safety measures, such as a corrosion-resistant coating (FIG. 2) or containment of the magnet in a corrosion-resistant case (FIG. 3). The corrosion-resistant material should be applied such that it does not significantly reduce the strength of the magnet however, and it should be resistant to frictional wear. Various corrosion resistant coatings and materials suitable for use in the oral cavity are known to those of skill in the art. As exemplified in FIGS. 7 and 8, a corrosion resistant sleeve (34) may be provided over the magnet (30) for protection in the oral cavity. The sleeve (34) is preferably a non-magnetic.

Figure 12A:
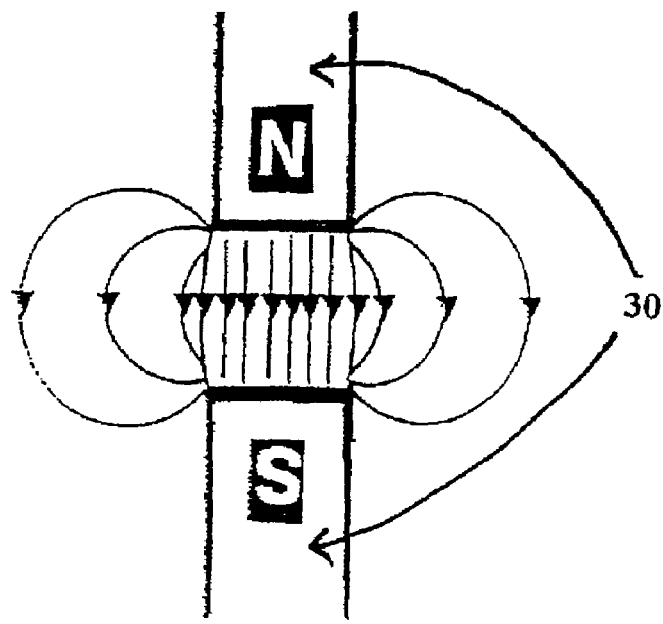
FIG. 12 illustrates magnetic fields, wherein FIG. 12a) shows magnetic field between two magnets, FIG. 12b) shows an open circuit configuration and FIG. 12c) shows a closed circuit configuration.
Figure 12B:
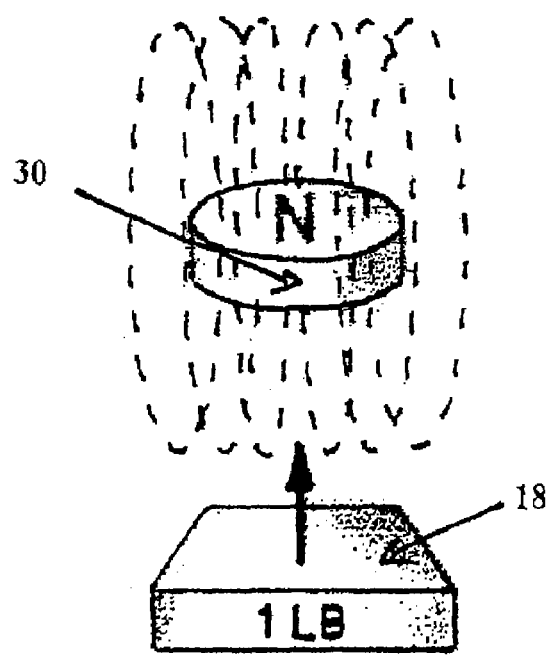
Figure 12C:
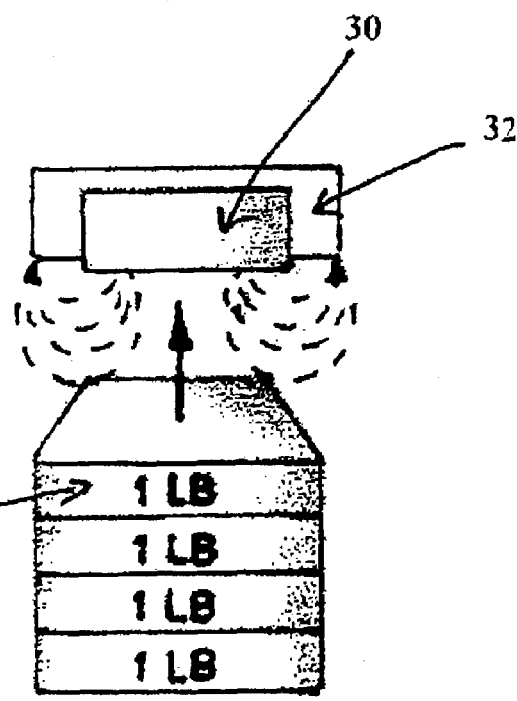

There are two types of magnetic circuits for magnetic attraction: an open circuit (FIGS. 12*a* and 12*b*) and a closed circuit (FIG. 12*c*). The attractive force of a closed magnetic circuit is about four times greater than that of an open magnetic circuit of the same volume. That said, in the case of an open circuit, the magnetic flux lines spread widely all over and the magnetic flux density becomes small at the attractive face. Whereas, in a closed magnetic circuit, magnetic flux lines are concentrated through the attractive face and the magnetic flux density increases (Ai and Shiau (eds.). New Magnetic Applications in Clinical Dentistry. Tokyo, Japan: Quintessence, 2004, pg. 33).

One embodiment of the magnetic dental appliance (10) employs a nickel plated $Nd_2Fe_{14}B$ disc magnet, of ⅜" diameter by 1/10" thickness, contained within a stainless steel ferromagnetic cup (32), which increases the magnetic force four-fold by bringing both poles of the magnet to grip on the same surface, as illustrated in FIG. 12*c*. This has been shown to provide a 5.0 lb. force against a stainless steel keeper plate. The nickel plating on such a magnet will eventually wear, which makes changing the magnet on a regular basis necessary, unless the magnet is housed in a protective corrosion-resistant casing, such as the retentive sleeve (34) exemplified in FIGS. 7 and 8.

Suitable magnets for use in accordance with the present invention include, but are not limited to, rare earth magnets. Magnet technology will continue to evolve resulting in new magnetic configurations that can be used with the magnetic dental appliance of the present invention.

Rare earth magnets come in a variety of sizes and shapes including discs, bars, rings, spheres and hemispheres. All are contemplated for use in accordance with the present invention. Disc magnets however, provide the highest usable surface area to mass ratio. The disc shape generally provides the greatest usable magnetic force for the money and is considered the preferred shape of magnet for use in accordance with the present invention. Various suppliers offer ferromagnetic cups for housing rare earth magnets. The ferromagnetic cup can be of any shape, such as square or circular, suitable for holding the magnet, and of any size suitable for attachment to or in the magnetic dental appliance (10).

As shown in FIGS. 1 and 8, the magnetic dental appliance (10) of the invention makes use of a magnetic component (14), preferably comprising a magnet (30), more preferably a rare earth magnet, in a ferromagnetic cup (32). When a magnet (30) is placed in a ferromagnetic cup (32), the cup magnifies the magnetic effect by eliminating the air gap (air is a poor conductor of magnetic fields) and bringing both poles of the magnet to grip on the same surface. This is similar in principle to a horseshoe magnet. As stated above, a rare earth magnet in a ferromagnetic cup provides four times the strength of a bare magnet. A ferromagnetic cup provides a disc magnet the optimal magnetic flux focus into the smallest gap area. In the preferred embodiment shown in FIG. 2, the magnet (30) is supported in a ferromagnetic cup (32), which is attached to the surface (36) of the upper arch attachment member (12). The magnetic component (14) can be provided on, in, or below the surface (36) of the upper arch attachment member (12) such that the magnet-attracted element (18) of the lower arch attachment member (16) is attracted by the magnet (14) when the appliance is worn by a subject.

The magnet could alternatively be provided in or on the lower arch attachment member (16), with the magnet-attracted element (18) being provided in or on the upper arch attachment member (12).

A preferred embodiment comprises a lower magnet-attracted element (18) in the form of an elongated stainless steel plate (17), as exemplified in FIG. 9, and an upper magnetic component (14) comprising a ferromagnetic magnet cup (32) of a corrosion resistant soft magnetic alloy. An exemplary alloy has a saturation magnetic flux density of 13,000 G or greater and permeability of at least 3000. A suitable material is ferritic stainless steel such as 19Cr-2Mo-0.1Ti steel (AUM 20™, Aichi Steel, Japan). As exemplified in FIGS. 7 and 8, the magnet (30) and ferromagnetic cup (32) are preferably covered by a non-magnetic, corrosion resistant sleeve (34), which is laser welded to the magnet cup (32) to seal the magnet between the sleeve (34) and the ferromagnetic cup (32). Of course, a seal could be provided by any means known in the art, including by simply embedding any gap formed between the sleeve (34) and the cup (32) in the material of the appliance or in methyl methacrylate resin.

A preferred material for the sleeve (34) is dental grade non-magnetic stainless steel 16Cr-12Ni-2Mo (SUS 316™). that is not significantly attracted to a magnet.

In this embodiment, a preferred magnet is a KJ/m³ class Neodymium Iron Boron (NdFeB) sintered magnet (Ai and Shiau (eds.). New Magnetic Applications in Clinical Dentistry. Tokyo, Japan: Quintessence, 2004, pp. 28).

In a first embodiment of the magnetic dental appliance (10) shown in FIG. 2a, the ferromagnetic cup (32) is attached to the upper arch attachment member(12) and all but the superior surface is enclosed with cold cure acrylic (FIG. 2b). In this configuration, it is possible with effort to relocate the ferromagnetic cup (32) anteriorly if the protrusion of the mandible has to be increased in order to open the airway further. A preferred embodiment shows two retentive wings (42) attached to the inferior surface of the ferromagnetic cup which extend laterally. In an improved embodiment, as shown in FIGS. 7 and 8, the retentive wings extend from the non-magnetic corrosion-resistant sleeve (34).

The retentive holes (44) in the wings (42) are used to affix the ferromagnetic cup (32) to the upper arch attachment member (12) in a fashion that will simplify the removal process by removing only the acrylic in the retentive holes (44). Once the ideal location of the magnetic component (14) is confirmed, i.e. by wearing the appliance, the wings (42) are buried in cold cure acrylic, preferably such that a platform (26) is formed around the magnetic component (14) and only the superior surface is exposed.

Figures 10, 10A, 10B, 10C, 10D:
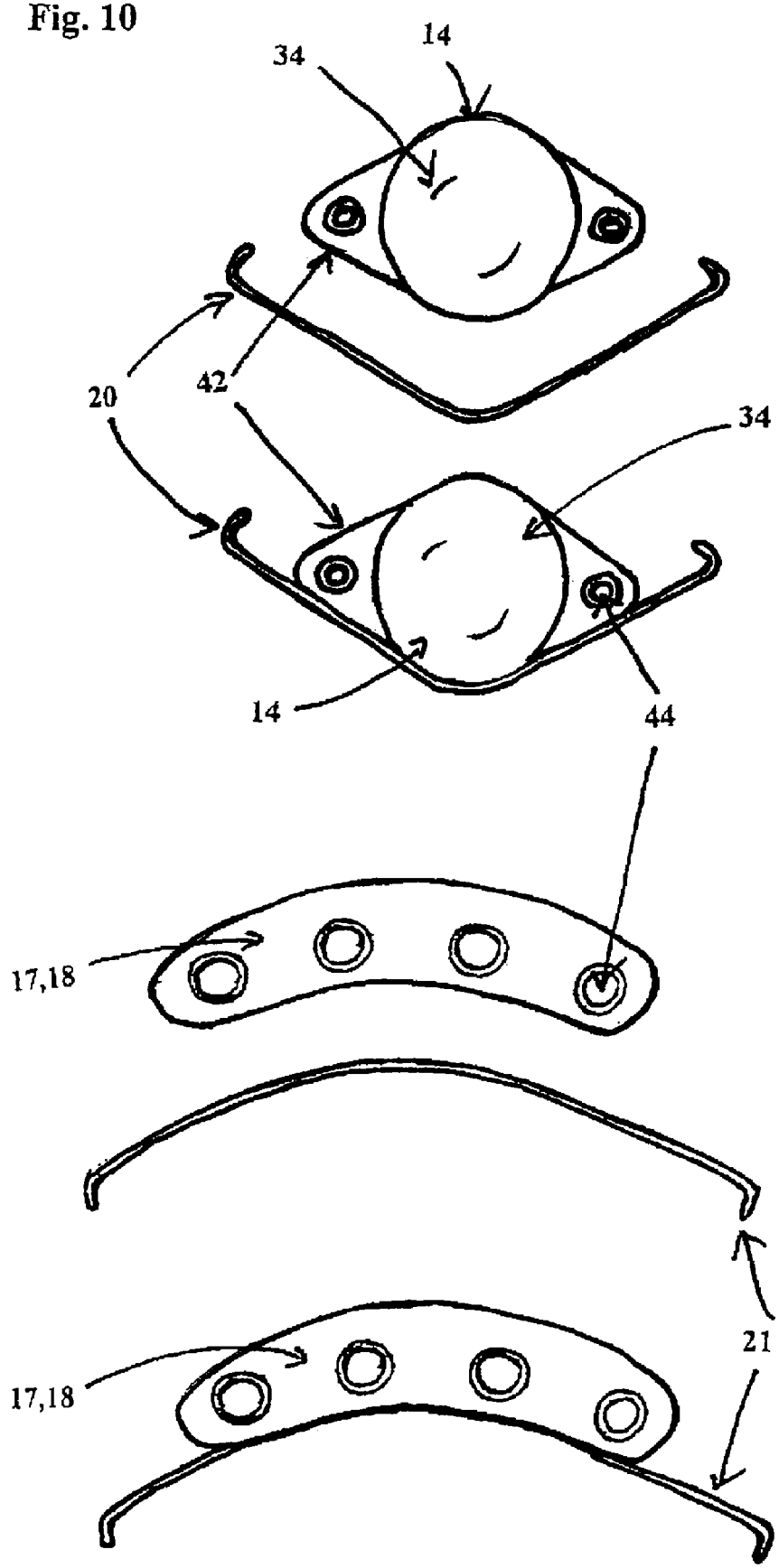
FIG. 10 shows the magnetic component and magnet-attracted element with one embodiment of an optional bilateral hook, wherein FIG. 10a) shows a bilateral hook separated from the magnetic component, FIG. 10b) shows a bilateral hook coupled to the magnetic component, FIG. 10c) shows a bilateral hook separated from the magnet-attracted element and FIG. 10d) shows a bilateral hook coupled to the magnet-attracted element.

The optional stainless steel bilateral hooks (20, 21), which are used to apply the Class II elastic forces, are also incorporated into this improved apparatus. As illustrated in FIGS. 10b and 10d, the hooks are preferably attached to the magnetic component (14) or the magnet-attracted element (18) such that the forward relocation of either component will automatically place the hooks in the proper location. Alternatively, the bilateral hooks (20 and 21) can be separated a distance from the components, as shown in FIGS. 10a and c.

If it is preferred to relocate the magnet-attracted element (18) instead of the magnetic component (14), then the acrylic is removed from the retentive holes (44) of the magnet-attracted element (18) and the component is removed and relocated, typically posteriorly. Attaching the stainless steel hooks (21) for the class II elastic force directly to the magnet-attracted element (18) will insure that the hooks will be in the correct location once the magnet-attracted element is re-located (FIG. 10).

It is believed that the opposed placement of the magnetic component (14) and magnet-attracted element (18) at about 70% to about 75% maximum protrusion, and the application of progressively greater class II elastic traction to encourage the mandible forward, is a highly biocompatible means of titration. While the need for relocating the magnet (30) or magnet-attracted element (18) can be satisfied, much of the adjustment can be accomplished by altering the elastic forces.

The magnet is preferably of a small size for maximum comfort to the patient wearing the appliance. An exemplary magnet has a diameter of about ⅜", although a magnet of a greater of lesser diameter would be suitable as well. The magnet is preferably sealed in a non-corrosive coating or protective casing.

Particularly suitable magnets for use in accordance with the magnetic dental appliance of the present invention would be similar to those described, for example, in U.S. Pat. No. 6,659,771, U.S. Pat. No. 5,678,998, U.S. Pat. No. 5,013,243 and U.S. Pat. No. 6,299,450, each assigned to Aichi Steel Corporation of Japan. However, the disclosed magnets are intended for use in retaining a removable denture prosthesis with a keeper of the same diameter, and are of a much smaller size (3.6 mm range).

The above-described represents a preferred embodiment of the magnetic component of the dental appliance of the invention. As a skilled person will appreciate, various types of magnets will be suitable for use in accordance with the present invention without departing from the main inventive concept.

Magnet-Attracted Element

Although a second magnet could be provided on the lower arch attachment member (16), for attracting the magnetic component (14) on the upper arch attachment member (12), it is preferred that the lower arch attachment member (16) comprise a magnet-attracted element (18) that is a non-magnet. The use of a non-magnet magnet-attracted element (18), such as an elongated metal plate (17), will improve safety as it prevents magnetic fields from being created in the oral cavity. Magnetic field production would occur if a second magnet were used instead of the non-magnet magnet-attracted element. This feature also permits movement of the magnetic component (14) along the non-magnet magnet-attracted element (18), thereby permitting translational and/or sagittal jaw movements for improved comfort to the patient.

The magnet-attracted element (18) can be created by providing a magnet-attracted material on, in, or below the surface (25) of the lower arch attachment member (16) so that that the lower arch attachment member (16) is attracted by the magnetic component (14) in the upper arch attachment member (12) when the appliance is worn by a subject.

In a preferred embodiment of the invention, as shown in FIG. 9, the magnet-attracted element (18) is in the form an elongated metal plate (17) attached to the lower arch attachment member (16). If a metal is selected that is subject to corrosion then the plate should be coated or otherwise protected to prevent corrosion in the oral cavity. The plate is preferably a stainless steel plate since stainless steel is resistant to corrosion. The elongated plate (17) extends along an anterior portion of the lower arch attachment member (16) to provide a length along which the lower arch attachment member (16) can travel while still magnetically engaging the magnetic component (14) in the upper arch attachment member (12). This advantageously allows translational movement of the mandible relative to the maxilla, for improved comfort, while the upper and lower arch attachment members (12, 16) remain magnetically engaged.

The magnet-attracted element (18) can be attached to the lower arch attachment member (16) by any means known in the art, for example, by the use of corrosion resistant screws or cement, or by a combination of retentive holes, as well as partially or totally embedding it in the lower arch attachment member (16) or in cold cure methyl methacrylate resin.

The embodiment exemplified in FIG. 9 uses four retentive holes (44) in the magnet-attracted element (18). These are drilled through the plate (17) and countersunk on the superior surface in order to provide retentive "tags". The initial attachment of the magnet attracted element (18) to the arch attachment member (16) is made using these retentive holes filled with cold cure methyl methacrylate. This allows the plate (17) to be removed and repositioned if desired by simply drilling the retentive tags out. Once the final treatment position is determined, the magnet-attracted element (18) can be attached to the arch attachment (16) member using the retentive holes (44) as well as encircling it or partially covering it with cold cure methyl methacrylate resin for added retention.

It is preferable that the superior surface of the magnet-attracted element (18) be exposed so that it can have intimate contact with the opposed magnetic component (14), as exemplified in FIGS. 2 and 3. This is because the magnetic attractive force decreases as the distance between the magnet (30) and magnet-attracted element (18) increases. This can be compensated for by using a stronger magnet, however it is desirable to use the weakest suitable magnet.

In an alternative embodiment (not shown), the magnet-attracted element can be provided by embedding an elongated metal plate, preferably a stainless steel plate, in the material of an arch attachment member during construction of the appliance.

The magnet-attracted element does not have to be elongated but this feature provides increased comfort to the patient since the patient is able to move the mandible back and forth in a translational motion with the magnet engaged, by sliding the magnet along the length of the magnet-attracted surface, thereby preventing discomfort that results when the jaws are rigidly held in a fixed relationship.

With particular reference to bruxing, the magnetic dental appliance (10) of the invention is unique in that the magnetic attraction between the magnetic component (14) on the upper arch attachment member (12) and the magnet-attracted element (18) on the lower arch attachment member (16) provides some resistance to translational, sagittal and vertical movements, however, permits all of these movements to occur to some degree against magnetic resistance and optional elastomeric forces. The presence of the optional class II elastomeric forces adds to the resistance to movement of the mandible against the maxilla. Therefore, in a bruxing patient, the need to grind and gnash the teeth (and in doing so exercising the musculature) is satisfied. Since the forces are dissipated by the magnetic and elastomeric forces, the dentition is protected and the appliance is exposed to less wear and tear. In most other titratable sleep apnea appliances, posterior bite pads are provided to protect the titrating mechanism or component. This allows greater forces to be generated by the bruxing patient. When contact occurs only on the anterior platform (26), as in the preferred embodiments disclosed herein, the degree of force that can be generated by the musculature is substantially decreased. FIGS. 2b, 3b.

Stainless steel is a particularly preferred material for the magnet-attracted element (18) due to its resistance to corrosion.

Auto-Centering

The elongated stainless steel plate (17) exemplified in FIGS. 1 and 9 provides a non-magnet magnet-attracted element (18) for magnetically engaging the magnetic component (14), which is preferably located in the anterior portion of the upper arch attachment member (12). This configuration results in a tendency for the magnetic component (14) to auto-centre on the surface of the magnet-attracted element (18). Thus, the magnetic component (14), located at the anterior portion of the upper dental arch (13), will automatically find the antero-posterior center of the elongated stainless steel plate (17) on the lower arch attachment member (16) where the antero-posterior magnetic force is zero. It is preferable that the diameter of the magnet be greater than the antero-posterior dimension of the magnet-attracted element, as illustrated in FIG. 11.

The use of a non-magnet metal plate (17) as the magnet-attracted element (18) results in automatic centering and re-centering of the magnetic component (14) on the plate (17). This can be achieved by a person of skill in the art in constructing the appliance.

As shown in FIG. 11, the magnet-attracted element (18) is preferably narrower in width (w) than the diameter (d) of the magnet (30) to encourage auto-centering. In a particularly preferred embodiment, the magnet-attracted element (18) is both longer in length (l) and narrower in width (w) than the diameter (d) of the magnet (30), as exemplified in FIG. 11, to provide a length along which the magnetic component (14) can glide while still engaging the magnet-attracted element (18).

In one exemplary embodiment, the magnet (30) has dimensions of ⅜" diameter by ⅒" thickness and the magnet-attracted element (18) is an elongated stainless steel plate (17) that is ¼" wide by 1/32" thick by 1¼" long.

Where the magnet is not a disc, the term "diameter" above can be replaced with width or length as appropriate. The concept of auto-centering remains the same.

The magnet-attracted element need not be provided "on" the surface of the lower arch, but could also be provided "in" the material of the lower arch, either by embedding a magnet-attracted material in the arch during construction or by composing a portion of the arch itself of a magnet-attracted material.

Titratability

Titration can be defined as the gradual forward movement of the mandible against the maxilla, without the necessity of making a new appliance each time the appliance needs to be adjusted. In an alternative preferred embodiment of the present invention, the magnetic dental appliance (10) is titratable to allow for adjustable, or indexed, positioning of the mandible relative to the maxilla.

In the exemplary embodiment of the appliance (10), it is noteworthy that the initial protrusive construction bite (being about 65% to about 75% of maximum protrusion) is likely to satisfy the needs of the majority of patients. A preferred embodiment uses a ⅜" disc magnet with an attractive force of 5 lb. The size and attractive force of the magnet (30) can be increased or decreased according to the needs of the individual patient (i.e. according to the strength of their musculature, tendency towards bruxism, etc) as will be appreciated by a person of skill in the art. The initial elastomeric force can be increased by substituting a smaller diameter elastomeric module (22) which will hold the mandible more rigidly but at the same time cause further protrusion of the mandible. If further adjustment is required then the magnet-attracted element (18) can be removed from the lower arch attachment member (16) and re-positioned further posteriorly. Another option would be to remove the magnetic component (14) from the upper arch attachment member (12) and position it more anteriorly.

Once the ideal configuration is found, the components of the device are attached to their respective arch attachment members (12 or 16) more securely. This is done, for example, by adding cold cure methyl methacrylate resin around their periphery in addition to their retentive holes (44). The present device is unique since adjustments can be made in at least four different ways:

1. Increase or decrease the magnetic force;
2. Increase or decrease the optional elastomeric force;
3. Reposition the magnet-attracted element (18); and/or
4. Reposition the magnetic component (14).

Having all of these options together in the magnetic dental appliance (10) of the invention provides the opportunity to truly customize the appliance to the patient's occlusion and comfort.

Titratable dental appliances have been described in the prior art, for example, in U.S. Pat. Nos. 5,427,117, 5,566,683 and 6,305,376 and 6,845,774. Many designs are uncomfortable to wear however, and are susceptible to breakage due to the presence of a rigid mechanical connection between the upper and lower arch attachment members.

Most patients experience a "straining" sensation when the mandible is initially advanced to a forward position that is sufficient to open the airway (40). This sensation is temporary and occurs because the mandible, TMJ, and supporting muscles are unaccustomed to the advanced position. The straining sensation subsides with wear. Some patients may therefore prefer to undergo gradual advancement of the mandible from a mild advanced position (i.e. 0 to about 1 mm) toward the maximum advanced position (i.e. about 6 mm or more) over repeated wear.

Using this appliance, the gradual forward romancing of the lower jaw may optionally be accomplished using progressively stronger orthodontic elastics followed by more rigid elastomeric modules. With the weaker elastic forces, the patient is allowed to express the lower jaw to the initial treatment position and allow the magnetic forces to engage. However, if the muscles and TMJ become sore, the patient can break the magnetic force by opening the mouth and allowing the lower jaw to retrude close to the centric occlusion position. As the elastomeric forces are gradually increased over several weeks, the degree of mandibular retrusion allowed is reduced to a negligible amount if necessary. The final elastomeric module should be replaced as needed (i.e. every few weeks), as they become stretched by use. The frequency of change is also governed by the amount of parafunctional activity (bruxism) that the appliance is subjected to.

The initial advanced position can be any desired position selected by a dentist or other qualified professional. As stated previously, the initial position is customarily about 65% to about 75% of maximum protrusion with the anterior teeth separated by about 5 to about 7 mm. For treatment of snoring or obstructive sleep apnea, the treatment advanced position is the position where the airway is opened sufficiently to allow proper air exchange and alleviate the symptoms of snoring or obstructive sleep apnea.

In an alternative titratable embodiment (FIG. 13), the ferromagnetic cup (32) may be housed in a directly titratable mechanism such as a serial screw mechanism, that allows incremental advancement of the ferromagnetic cup (32) on the upper arch attachment member (12) relative to the magnet-attracted element (18) on the lower arch attachment member (16). A support member (60) is provided, which comprises a titration plate (70) with progressive threaded screwholes (72) for adjusting the position of the ferromagnetic cup (32). The ferromagnetic cup (32) has a countersunk hole (74) in its base through which a short screw (76) attaches the ferromagnetic cup (32) to the titration plate (70). Titration of the magnet (30) occurs by repositioning the ferromagnetic cup (32) on the titration plate (70) in the saggital plane. Adjustment of the magnet (30) correspondingly adjusts the positioning of the mandible relative to the maxilla when the appliance is worn by a subject and the magnetic component is engaged. A corrosion resistant cap (38) is then positioned over the support member (70), preferably in a sealing engagement, to house the magnet (30).

Figure 14:
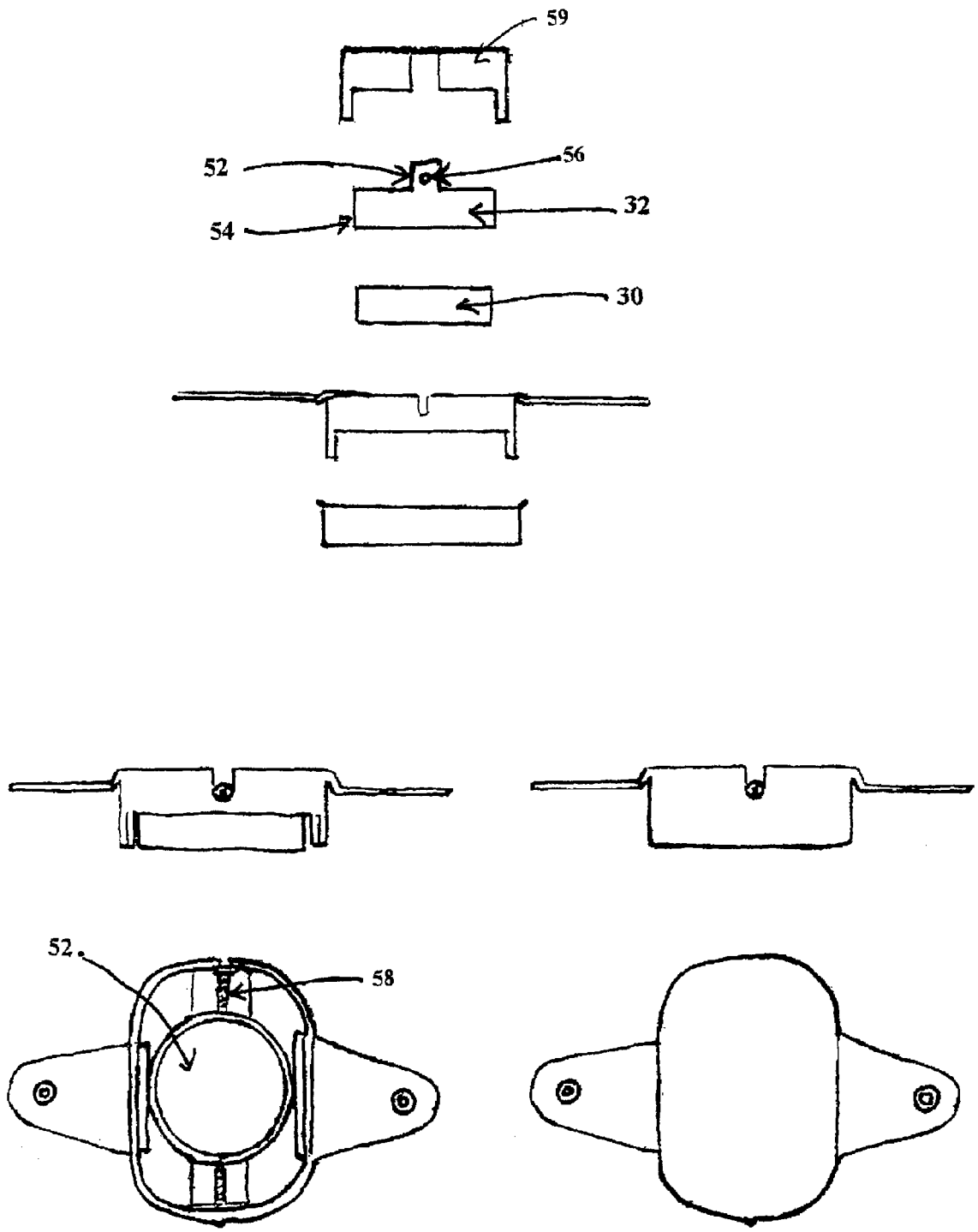
FIG. 14 illustrates a titratable wormscrew mechanism.

In a second alternative embodiment (FIG. 14), the ferromagnetic cup (32) includes an extension at its base (52) and an upstanding wall (54) for supporting the magnet (30). A lateral hole with a threaded bore (56) is provided in the extension (52) of the ferromagnetic cup (32) for receiving a wormscrew (58). The wormscrew (58) is used to fasten the ferromagnetic cup (32) to a support member (59) via the lateral hole with threaded bore (56). The turning of the wormscrew advances the location of the ferromagnetic cup (32) in a saggital direction.

In a further embodiment, not shown, titratability is provided by adjusting the relative antero-posterior positioning of the magnet-attracted element.

Various other means of providing a titratable dental appliance in accordance with the present invention may be adapted from the prior art and will become apparent to those of skill in the art. Uninventive variants are considered within the scope of the present invention.

Elastic Attachments

As described above, elastic modules (22) may be added to the appliance (10) to further urge the mandible forward. Elastic modules (22) would be especially useful during the initial stage of wearing the appliance when the patient is not accustomed to protruding the mandible, or during times when a patient is at increased risk of apnea or bruxing, for example, after alcohol consumption or during periods of extreme stress or fatigue. In one embodiment, bilateral stainless steel hooks (20, 21) are applied on the buccal segments of the upper and lower arch attachment members (12, 16) and elastic modules (22) of different strengths can be selected and applied as needed. Elastic modules (22) are preferably applied in a class II configuration as shown in FIGS. 1b, 4b, 5b, 6b and 6c. Class II elastics are known in the art and have been used in orthodontics for over 60 years.

Kit

A kit may be produced, which includes the magnetic dental appliance of the present invention, in assembled or unassembled form, together with instructions for assembly and/or use in the treatment of snoring, sleep apnea, bruxism, headaches, TMJ problems or myofascial pain. The kit may further include studs and/or elastics for attachment to the appliance. Preferably, the arches are custom-fit dental arches prepared by a dentist or other skilled professional and provided in the kit to the patient.

Construction of the Magnetic Dental Appliance

In accordance with the preferred embodiment of the magnetic dental appliance (10) of the invention, a subject is fitted for custom arch attachment members (12, 16) in the usual manner, and custom arch attachment members (12, 16) are prepared for making the appliance (10).

The arch attachment members (12, 16) can be custom fabricated on a set of stone dental casts, as is known in the art. In such a construction, a duplicate set of stone dental casts are mounted on a semi-adjustable articulator. The upper dental cast is mounted using a facebow transfer. The lower dental cast is mounted against the upper in centric occlusion, i.e. the casts are hand-articulated or a wax or silicone centric occlusion record is used to articulate the casts.

A protrusive record is obtained from the patient at about 60% to about 80%, preferably about 70% to about 75%, maximum protrusion. Using this protrusive record, the condylar inclination can be set on the semi-adjustable articulator. The cast positions are marked so that they can be positioned there when the arch attachment members (12, 16) are placed on the upper and lower casts and the magnetic component (14) and magnet-attracted element (18) are attached to their respective arch attachment members (12, 16) such that they oppose one another and the magnetic component (14) is centered on the magnet-attracted element (18). In one embodiment, Retentive Modified Arrowhead (Adam's) clasps are optionally fabricated from stainless steel orthodontic wire, for example, 0.7 mm stainless steel orthodontic wire, for the lower second bicuspids and the upper first bicuspids, bi-laterally, to provide added retention, not shown.

The magnet (30), preferably in a ferromagnetic cup (32), is attached to the upper arch attachment member (12), preferably using cold cure methyl methacrylate resin. In an alternate embodiment, the magnet (30) or magnetic component (14) may be embedded in the arch attachment member during construction. A magnet-attracted element (18), preferably an elongated stainless steel plate (17), as shown in FIG. 9, is attached to the lower arch attachment member (16), also using cold cure methyl methacrylate resin. Alternatively, the magnet attracted element (18) is embedded in the lower arch during construction to provide a magnet-attracted surface on the lower arch attachment member (16). If the magnet or magnet-attracted material are embedded in the arch attachment members during construction, they should be embedded sufficiently close to the outer surface of the arches to provide adequate magnetic attraction between the upper and lower arches.

Operation of the Magnetic Dental Appliance

The magnetic dental appliance of the invention is very simple to operate. Referring to the exemplary embodiment shown in FIG. 1, the upper and lower arch attachment members (12, 16) are fitted snuggly over the upper and lower teeth of the subject, also see FIG. 4. The close fit ensures that the arches stay in place over the teeth during sleep and when talking. The retention may be increased by placing modified arrowhead ("Adams") clasps bi-laterally on the upper first bicuspids and the lower second bicuspids. It is recommended that the appliance be removed while eating. The magnet-attracted element (18) on the lower arch attachment member (16), preferably a stainless steel plate (17), provides a non-magnet magnet-attracted surface on the lower arch attachment member (16) that is attracted to the magnetic component (14) on the upper arch attachment member (12). When the subject closes the mouth, the magnetic component (14) and magnet-attracted element (18) become magnetically engaged. When the mandible is advanced, the airway (40) is opened (FIG. 5), which provides relief to subjects prone to snoring and mild to moderate obstructive sleep apnea. A patient suffering from TMJ or myofascial pain may also experience relief from the minimal repositioning of the mandible in the forward position with the appliance functioning as an anterior de-programmer. For patients that are bruxers, the arch attachment members will provide a protective surface to prevent or reduce wear on the teeth which occurs during grinding.

It is not necessary that the appliance advance the mandible. This will depend on the particular application of the appliance. It is well within the ability of a person skilled in the art to determine the degree, if any, to which the mandible should be advanced for treatment. The range can vary from no protrusion to near maximum protrusion, depending on what the appliance is being used for. For bruxism or MPDS (myofacial pain dysfunction syndrome) without obstructive sleep apnea, the degree of protrusion is generally from 0% to about 10% of maximum protrusion. In the treatment of some types of TMJ problems (eg. Retrodiscitis), the mandible is generally advanced between about 5% and about 10% of maximum protrusion if no obstructive sleep apnea is being treated.

For the treatment of obstructive sleep apnea in conjunction with the above ailments, the treatment range is generally between about 70% and about 75% of maximum protrusion initially. This can be increased to as much as 100% of maximum protrusion if needed.

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A removable magnetic dental appliance, comprising:
    an upper arch attachment member for removably engaging at least a portion of the upper dentition;
    a lower arch attachment member for removably engaging at least a portion of the lower dentition;
    a magnetic component comprising a magnet positioned anteriorly on one of the upper arch attachment member or the lower arch attachment member; and
    an elongated non-magnet magnet-attracted element on the other of the upper or lower arch attachment member for magnetic engagement with the magnetic component when the upper arch attachment member and the lower arch attachment member are substantially vertically aligned, the magnetic dental appliance being shaped and constructed to permit translational or sagittal movement of the upper arch attachment member relative to the lower arch attachment member when the magnetic component and the elongated non-magnet magnet-attracted element are magnetically engaged, the elongated non-magnet magnet-attracted element providing a length along which the magnetic component can travel while remaining magnetically engaged with the elongated non-magnet magnet-attracted element.

2. The magnetic dental appliance of claim 1, wherein the magnet is a rare earth magnet.

3. The magnetic dental appliance of claim 2, wherein the magnetic component further comprises a ferromagnetic cup and wherein the magnet is housed in the ferromagnetic cup.

4. The magnetic dental appliance of claim 3, wherein the magnetic component further comprises a corrosion resistant sleeve coupled to the ferromagnetic cup in sealing engagement therewith, the sleeve comprising retentive wings for attaching the magnetic component to the upper arch attachment member.

5. The magnetic dental appliance of claim 4, wherein the sleeve is non-magnetic.

6. The magnetic dental appliance of claim 1, wherein the magnetic component and the elongated non-magnet magnet-attracted element are positioned relative to each other such that when the magnetic component and the elongated non-magnet magnet-attracted element are engaged, the mandible of a subject wearing the appliance is advanced.

7. The magnetic dental appliance of claim 6, wherein the mandible is advanced from about 70% to about 75% maximum protrusive range between the mandible and the maxilla.

8. The magnetic dental appliance of claim 6, wherein the mandible is advanced from about 0% to about 10% maximum protrusive range between the mandible and the maxilla.

9. The magnetic dental appliance of claim 6, which is capable of treating snoring, sleep apnea, temporomandibular joint pain, temporomandibular joint inflammation, myofascial pain or bruxism.

10. The magnetic dental appliance of claim 1, wherein the magnet is coupled to the upper arch attachment member and the elongated non-magnet magnet-attracted element is coupled to the lower arch attachment member.

11. The magnetic dental appliance of claim 10, wherein a platform is provided lingual to the magnetic component, the platform for preventing the lower arch attachment member from being positioned behind the upper arch attachment member when the appliance is worn by a subject.

12. The magnetic dental appliance of claim 1, wherein the upper arch attachment member and the lower arch attachment member are each custom-fitted.

13. The magnetic dental appliance of claim 12, wherein the upper arch attachment member and the lower arch attachment member are composed of pressure formed thermoactive acrylic resin or injection moulded thermoactive acrylic resin.

14. The magnetic dental appliance of claim 1, wherein the elongated non-magnet magnet-attracted element is a stainless steel plate.

15. The magnetic dental appliance of claim 14, wherein the stainless steel plate has an antero-posterior width less than the diameter of the magnetic component to encourage auto-centering of the magnetic component on the plate.

16. The magnetic dental appliance of claim 1, further comprising a first bilateral hook on the upper arch attachment member and a second bilateral hook on the lower arch attachment member.

17. The magnetic dental appliance of claim 16, further comprising a removable elastic module for attachment between one hook of each of the first bilateral hook and the second bilateral hook in a class II configuration.

18. The removable dental appliance of claim 1, wherein at least one of the magnetic component and the elongated non-magnet magnet-attracted element is titratable.

19. The magnetic dental appliance of claim 1, which is capable of treating snoring, sleep apnea, temporomandibular joint pain, temporomandibular joint inflammation, myofascial pain or bruxism.

* * * * *